United States Patent [19]

Ikeyama

[11] Patent Number: 4,706,072
[45] Date of Patent: Nov. 10, 1987

[54] HUMAN CONDITION MONITORING AND SECURITY CONTROLLING APPARATUS ON A ROAD-VEHICLE

[75] Inventor: Takeshi Ikeyama, Tokyo, Japan

[73] Assignee: Aisin Seiki Kabushiki Kaisha, Aichi, Japan

[21] Appl. No.: 676,326

[22] Filed: Nov. 29, 1984

[30] Foreign Application Priority Data

| Nov. 30, 1983 | [JP] | Japan | 58-225794 |
| Nov. 30, 1983 | [JP] | Japan | 58-225795 |
| Nov. 30, 1983 | [JP] | Japan | 58-225796 |
| Dec. 20, 1983 | [JP] | Japan | 58-240530 |
| Dec. 22, 1983 | [JP] | Japan | 58-242788 |
| Mar. 13, 1984 | [JP] | Japan | 59-48457 |

[51] Int. Cl.⁴ .................................... G08B 23/00
[52] U.S. Cl. .................................. 340/576; 128/666; 340/575
[58] Field of Search ............ 340/576, 575, 573; 128/702, 687, 666, 639

[56] References Cited

U.S. PATENT DOCUMENTS

| 3,731,672 | 5/1973 | McIntosh | 128/703 |
| 3,980,075 | 9/1976 | Heule | 128/666 |
| 4,063,551 | 12/1977 | Sweeney | 128/666 |
| 4,163,447 | 8/1979 | Orr | 128/666 |
| 4,210,905 | 7/1980 | Coons | 340/575 |
| 4,234,051 | 11/1980 | Morris, Jr. | 340/575 X |
| 4,340,813 | 7/1982 | Sauer | 250/221 |
| 4,353,152 | 10/1982 | O'Connor | 128/666 X |
| 4,485,375 | 11/1984 | Hershberger | 340/576 |
| 4,540,979 | 9/1985 | Gerger | 340/576 |
| 4,572,207 | 2/1986 | Yoshimi | 128/639 X |

Primary Examiner—James L. Rowland
Assistant Examiner—Jeffery A. Hofsass
Attorney, Agent, or Firm—Sughrue, Mion, Zinn, Macpeak & Seas

[57] ABSTRACT

There is provided an apparatus which decides the presence or absence of an anomaly by detecting the gripped state of a steering wheel by the driver steering a road-vehicle, or by measuring fluctuations in heart rate and heartbeat period of the driver, and which issues an alarm of "Take a rest", etc. or controls the vehicle speed to be lowered, if there occurs any anomaly. Detecting means is attached to a steering wheel, steering wheel cover or a band-shaped member. The detecting means comprises a plurality of reflection type optical sensors which are each composed of a light emitting element and one or more light receiving elements, and which are set in such proper arrangement and orientation as permitting detection in any of various conditions.

16 Claims, 44 Drawing Figures

HUMAN CONDITION MONITORING AND SECURITY CONTROLLING APPARATUS ON A ROAD-VEHICLE

BACKGROUND OF THE INVENTION

The present invention relates to a human condition and security controlling apparatus on road-vehicles for detecting the condition of a driver and taking a given security action in accordance with the detected result.

Taking the case of a driver for automobiles, for example, the possibility of accidents is largely dependent on the health condition and the degree of fatigue of the driver. More specifically, if the driver should be seized with a heart attack during driving by way of example, he would lose the capability of driving, thus resulting in the very high possibility of accidents. Also, if the driver falls into a doze due to accumulated fatigue, an accident may occur with high possibility. Furthermore, accumulation of fatigue tends to reduce efficiency and impair health in the work and routine life.

SUMMARY OF THE INVENTION

A first object of the present invention is to provide a human condition and security controlling apparatus on road-vehicles for detecting the health condition, drive operation, etc. of a driver for road-vehicles and then automatically taking a given security action if any anomaly is detected.

To achieve the above object, the present invention uses status detecting means for detecting driver's hands, and information output from the status detecting means is monitored to actuate security means on the road-vehicle, such as a display or alarm sound generator, in accordance with the monitored result.

More specifically, the condition of the driver is decided by obtaining a heartbeat signal from his hands to be detected, or by detecting a signal corresponding to whether or not a steering wheel is firmly gripped by the hands.

Heart rate is one of barometers which indicate the condition of human health. As apparatus for measuring heart rate, there are known a heartbeat measuring device for medical treatment and a portable small-sized heartbeat meter. The small-sized heartbeat meter is portable to any desired place, but has low measurement accuracy. Even if it is carried on a road-vehicle, heart rate of the driver has to be measured during a stop of the road-vehicle. More specifically, the heartbeat meter of this type makes a measurement in such a state that a reflection type photo sensor is put against the pad of a driver's finger, and that the sensor and the finger are both covered with a black sponge, etc. to avoid an influence of lights coming from the outside. In addition, if the positional relationship between the finger and the sensor is changed, measurement is interrupted and hence the finger may not be moved. As a result, the driver can not drive the road-vehicle during measurement of heart rate.

Therefore, a second object of the present invention is to provide a human condition and security controlling apparatus on road-vehicles which makes it possible to automatically measure a heartbeat even when a driver is normally driving a car.

To achieve the above object, in a preferred embodiment of the present invention, there is employed status detecting means so structured that a plurality of light receiving elements are arranged about a light emitting element to surround the same, and optical axes of the light emitting and receiving elements are directed substantially in the same direction. Further, in another preferred embodiment of the present invention, a plurality of detectors each comprising light emitting means and light receiving means are employed to form an annular unit, and this unit is fitted in plural number to surround the grip portion of a steering wheel. By so doing, it becomes possible to detect a heartbeat signal, etc. from the palm or a part of the arm, and this eliminates the limitation which is otherwise imposed in case of detecting a heartbeat signal from the fingertip. Thus, the heartbeat can be automatically measured while the driver is driving a car in the normal state.

When arranging the status detecting means on a steering wheel by way of example, to permit status detection during actual driving it is required to dispose a number of status detection means along the grip portion of the steering wheel, thereby allowing to detect the status when the steering wheel is gripped at any position. However, if a number of status detecting means are connected in parallel to obtain a signal, a level of noise is raised due to an influence of lights coming from the outside, etc. because there are less number of detecting means which actually produce the desired signal, whereby the S/N (signal/noise) ratio is too lowered to make status detection.

Therefore, a third object of the present invention is to provide a human condition and security controlling apparatus on road-vehicles which is capable of detection wherever the driver grips a steering wheel, and in which lights coming from the outside will never cause any malfunction.

To achieve the above object, in a preferred embodiment of the present invention, a number of status detecting means are disposed, output levels of the individual detecting means are sequentially monitored to find those detecting means which produce a desired signal, and such detecting means are selectively connected to a measuring section for measurement. With this arrangement, since selection of the status detecting means is automatically made, operation is simple, and since the detecting means to be used are selected upon actually monitoring outputs of the detecting means, there occurs no selection error.

In the above case, if the detecting means are formed of optical sensors, an output of each sensor exhibits a level corresponding to the sum of a desired signal and extraneous lights, i.e., noise, and the intensity of extraneous lights is largely different depending on its position on the steering wheel. Accordingly, when making a decision upon comparison of the detected signal level with a given threshold value, erroneous detection may be resulted if setting of the threshold value is not appropriate. Thus, more preferably, levels of every adjacent detecting means are compared with each other to find the beginning one and the ending one of the detecting means to be used in accordance with the resultant difference in level, and those detecting means in such a range are all selected. Since it is assumed that an influence of extraneous lights acts upon the adjacent detecting means in a similar manner, the above arrangement can surely offset such influence of extraneous lights.

If the status detecting means of the human condition and security controlling apparatus on road-vehicles are buried in a steering wheel, the steering wheel has to be also newly attached, i.e., exchanged, in need of newly attaching the apparatus.

Therefore, a fourth object of the present invention is to provide a human condition and security controlling apparatus on road-vehicles which allows the detection of the status even when the driver is driving a road-vehicle, and which is easy in attaching and detaching.

To achieve the above object, in a preferred embodiment of the present invention, the status detecting means are fitted to a steering wheel cover. This makes easy attaching and detaching of the human condition and security controlling apparatus on road-vehicles, because the steering wheel cover can be attached and detached with more ease.

Further, if the status detecting means fitted on the steering wheel cover is connected to the apparatus body with wires, this intervenes operation for driving. Thus, in a preferred embodiment, there are provided signal transmitting means for sending a signal from the status detecting means carried on an electric wave, and signal receiving means for receiving the electric wave output from the transmitting means to demodulate a given status signal. This permits dispensing with wires to be used for connecting between each status detecting means and the apparatus body. Furthermore, in a preferred embodiment, the signal transmitting means is constituted so as to be detachably attached to a spoke of steering wheel.

In addition, to achieve the above fourth object, in another preferred embodiment of the present invention, the status detecting means are fitted to a band-shaped support member, so that the status detecting means may be fitted to a part of the arm or so. With this arrangement, the status detecting means are easily attached and detached, and the status can be detected even during driving. In this embodiment, there are provided signal transmitting means for transmitting a signal from the status detecting means carried on an electric wave, and signal receiving means for receiving the electric wave output from the transmitting means to demodulate a given status signal. By so doing, the status detecting means can be disposed in a position remote from the apparatus body, and wires for connecting them can be dispensed with.

If any anomaly can be detected when it occurs in the driver's condition while driving a road-vehicle, etc., it becomes possible to take a given security action before occurrence of accidents to thereby prevent such possible accidents in advance.

Therefore, a fifth object of the present invention is to provide a human condition and security controlling apparatus which can detects whether or not the driver is in the normal condition, and which automatically takes a security action if any anomaly is detected.

To achieve the above object, in a preferred embodiment of the present invention, the gripped state of the steering wheel is detected using status detecting means, and security means is actuated in accordance with the detected state.

More specifically, in the event the driver is seized with a heart attack during driving, or in the event the driver falls into a doze during driving, he generally releases a handle, i.e., steering wheel, or grips the same with weakened forces. Accordingly, the presence or absence of anomaly in the driver's condition can be decided by detecting the gripped state of the steering wheel.

In this case, reflection type optical sensors, pressure sensors, temperature sensors, potential sensors, capacitance sensors, etc. can be used as status detecting means. However, since the driver often wears gloves when driving, and since the steering wheel is differently gripped depending on individual drivers, the gripped state of the steering wheel can not be always detected depending on some combinations of the types of sensors and usage conditions. Thus, in a preferred embodiment of the present invention, the status detecting means are formed of reflection type optical sensors. In case of using reflection type optical sensors, the decision level is simply adjusted in accordance with detecting conditions such as whether the driver's hands are placed on the steering wheel, or whether the steering wheel is gripped with forces greater than a predetermined value. Further, a heartbeat signal can be obtained by processing a signal output from the optical sensor, so that the sensor may be used also for other purposes such as making heartbeat measurement on road-vehicles.

Other objects and arrangements of the present invention will be apparent from the following description with reference to the accompanying drawings.

BRIEF DESCRIPTION OF THE DRAWINGS

FIG. 2b is a sectional view taken along the line IIb—IIb in FIG. 2a;

FIG. 2c is a sectional view taken along the line IIc—IIc in FIG. 2a;

FIG. 3b is an electric circuit diagram showing a part of FIG. 3a;

FIG. 4 is a block diagram showing the configuration of a video memory VRAM1 in FIG. 3a;

FIG. 5 is a flow chart schematically showing operation of a microcomputer CPU in FIG. 3a;

FIG. 7b is an enlarged sectional view taken along the line VIIb—VIIb in FIG. 7a;

FIG. 7c is an enlarged sectinal view taken along the line VIIc—VIIc in FIG. 7a;

FIG. 7d is an electric circuit diagram showing a part of an electric circuit to which connected are sensors fitted to the steering wheel shown in FIG. 7a;

FIG. 8b is an enlarged sectional view taken along the line VIIIb—VIIIb in FIG. 8a;

FIG. 8c is an enlarged sectional view taken along the line VIIIc—VIIIc in FIG. 8a;

FIGS. 9a, 9b and 9c are block diagrams showing an electric circuit to which connected is the steering wheel shown in FIG. 8a;

FIGS. 10a and 10b are flow charts schematically showing operation of a microcomputer CPU shown in FIG. 9a;

FIG. 11a is a graph showing one example of output levels from a part of optical sensors shown in FIG. 9a;

FIG. 12b is a partially enlarged view of FIG. 12a;

FIGS. 13a and 13b are plan views showing wheel on which fitted is the steering wheel cover shown in FIG. 12a;

FIG. 17b is a sectional view taken along the line XVIIb—XVIIb in FIG. 17a;

DESCRIPTION OF PREFERRED EMBODIMENTS

In the following, preferred embodiments of the present invention will be described with reference to the drawings.

Figure 1:
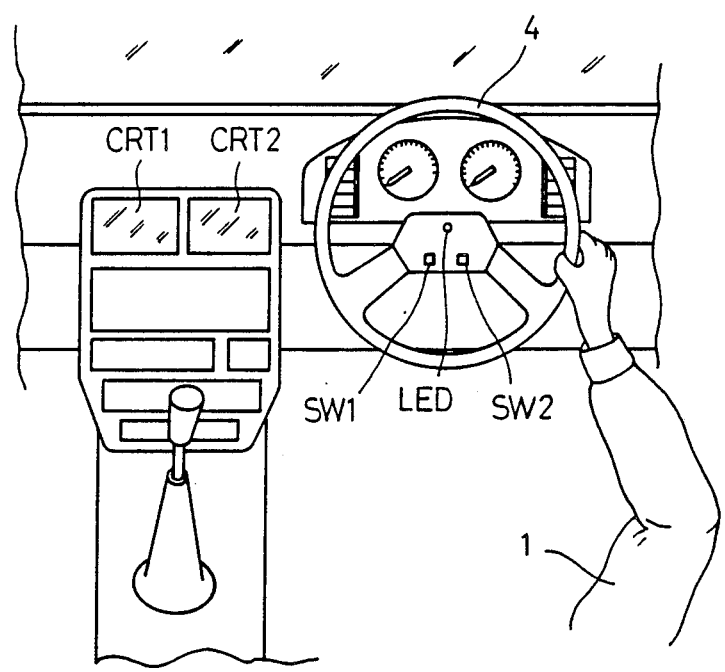
FIG. 1 is a front view showing the vicinity of a driver's seat of a road-vehicle loaded with a heart rate meter according to one embodiment of the present invention.

FIG. 1 shows the vicinity of a driver's seat of a road-vehicle loaded with a heartbeat meter according to one embodiment of the present invention. Referring to FIG. 1, a steering wheel 4 is equipped at the center thereof with a start switch SW1 for instructing to start the heartbeat measurement, a cancel switch SW2 for instructing to cancel the measurement, and a light emitting diode LED for providing an indication corresponding to the heartbeat. On the left side of the steering wheel 4, there are provided two Brown tube display units CRT1 and CRT2.

Figure 2A:
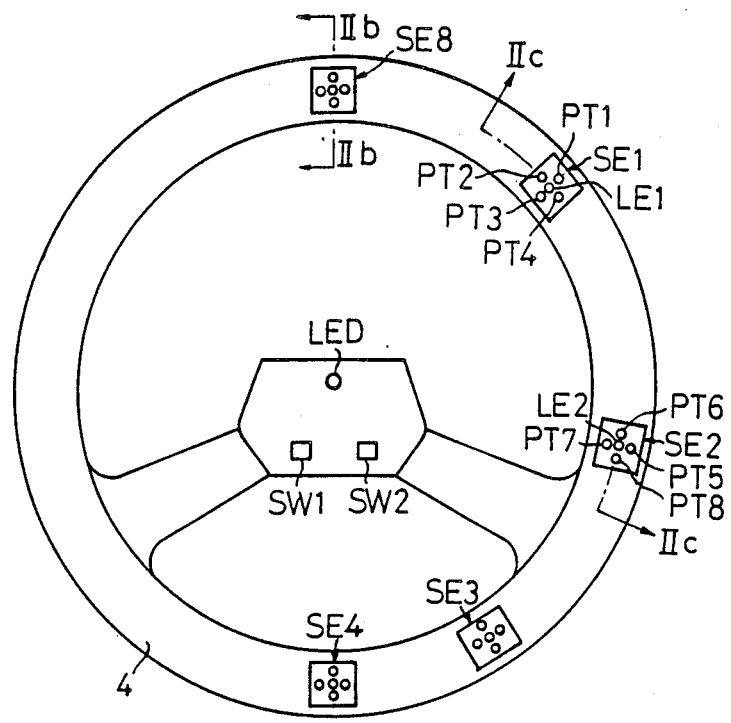
FIG. 2a is an enlarged plan view showing a steering wheel 4 of the road-vehicle shown in FIG. 1.
Figure 2B:
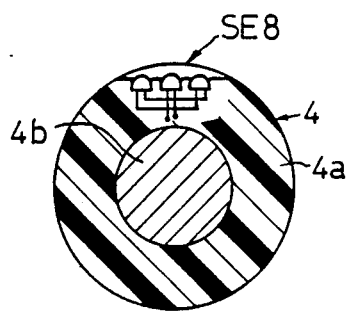
Figure 2C:
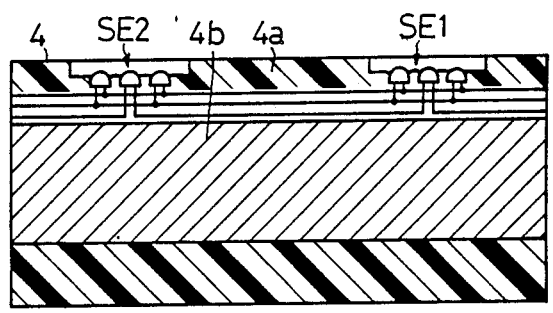

The steering wheel 4 is shown in more detail in FIGS. 2a, 2b and 2c. Referring now to these figures, reflection type optical sensors SE1, SE2, . . . , SE8 are arranged on the upper surface of the steering wheel 4 in a dispersed relation from one another. Each of the optical sensors comprises one light emitting diode (LE1) and four photo transistors (PT1-PT4) arranged around the former. The light emitting diode equipped in each optical sensor is formed of an infrared light emitting diode which is adapted to emit a beam of light in an infrared range. One light emitting diode and four photo transistors included in each optical sensor are arranged to have their axes extending in the same direction (i.e., toward above the steering wheel 4). The steering wheel 4 is composed of an iron core 4b and a resin 4a covering the former, and the individual optical sensors are secured in the portion of the resin 4a. Electric wires led from each optical sensor are connected to an electronic circuit housed in a panel at the center of the steering wheel 4 after passing through the inside of the resin 4a.

Figure 3A:
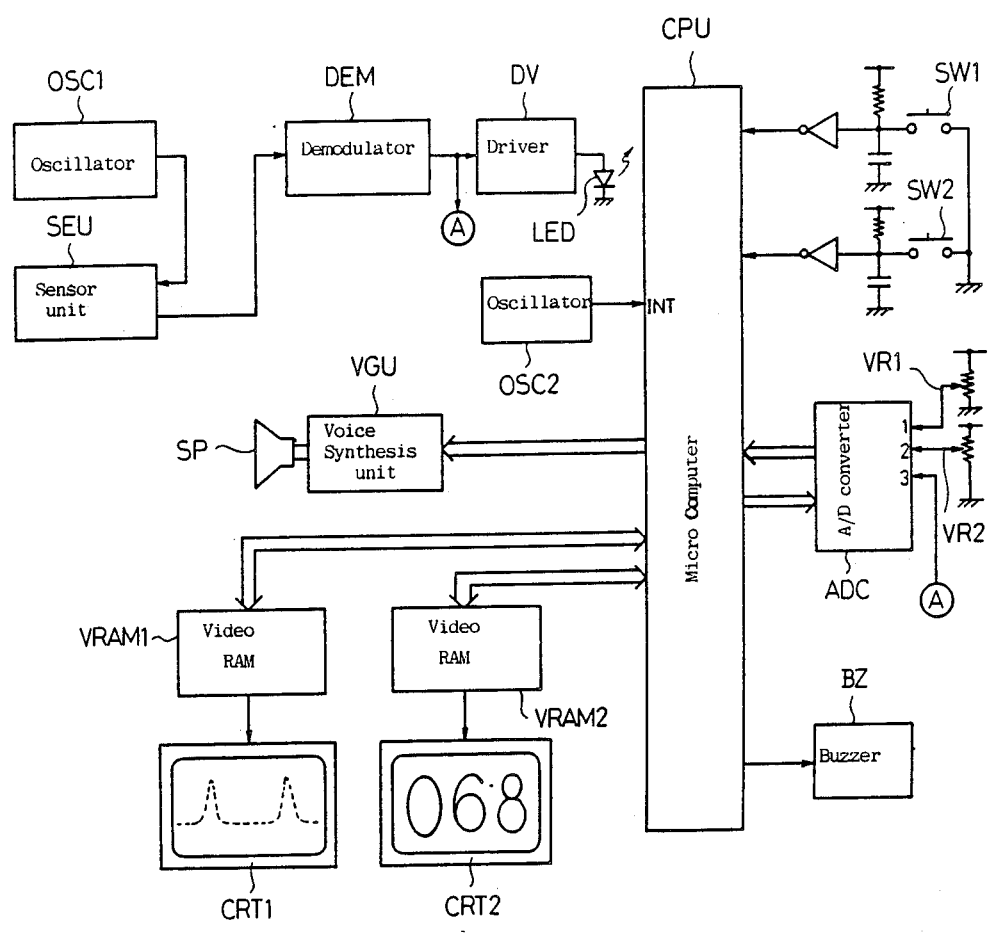
FIG. 3a is a block diagram showing an apparatus loaded on the road-vehicle shown in FIG. 1.

FIG. 3a schematically shows the circuit configuration of the heartbeat meter loaded on the road-vehicle shown in FIG. 1. Description will now be made with reference to FIG. 3a. It is a microcomputer CPU that controls the entire circuit. Connected to the microcomputer CPU are an oscillation circuit OSC2, voice synthesis unit VGU, video memories VRAM1 and VARM2, buzzer BZ, A/D converter ADC, key switches SW1 and SW2, etc. A circuit interposed between the key switches SW1, SW2 and the CPU is of a waveform shaping circuit. A speaker SP is connected to an output terminal of the voice synthesis unit VGU, and Brown tube display units CRT1 and CRT2 are connected to the video memories VRAM and VRAM2, respectively. Variable resistors VR1 and VR2 for setting reference levels are respectively connected to input terminals 1 and 2 of the A/D converter ADC, while an output terminal of a demodulation circuit DEM is connected to an input terminal 3 of the ADC. An output terminal of the demodulation circuit DEM is connected to the light emitting diode LED for indication through a driver DV. An output terminal of the oscillation circuit OSC1 is connected to a sensor unit SEU, an output terminal of which in turn is connected to an input terminal of the demodulation circuit DEM.

Figure 3B:
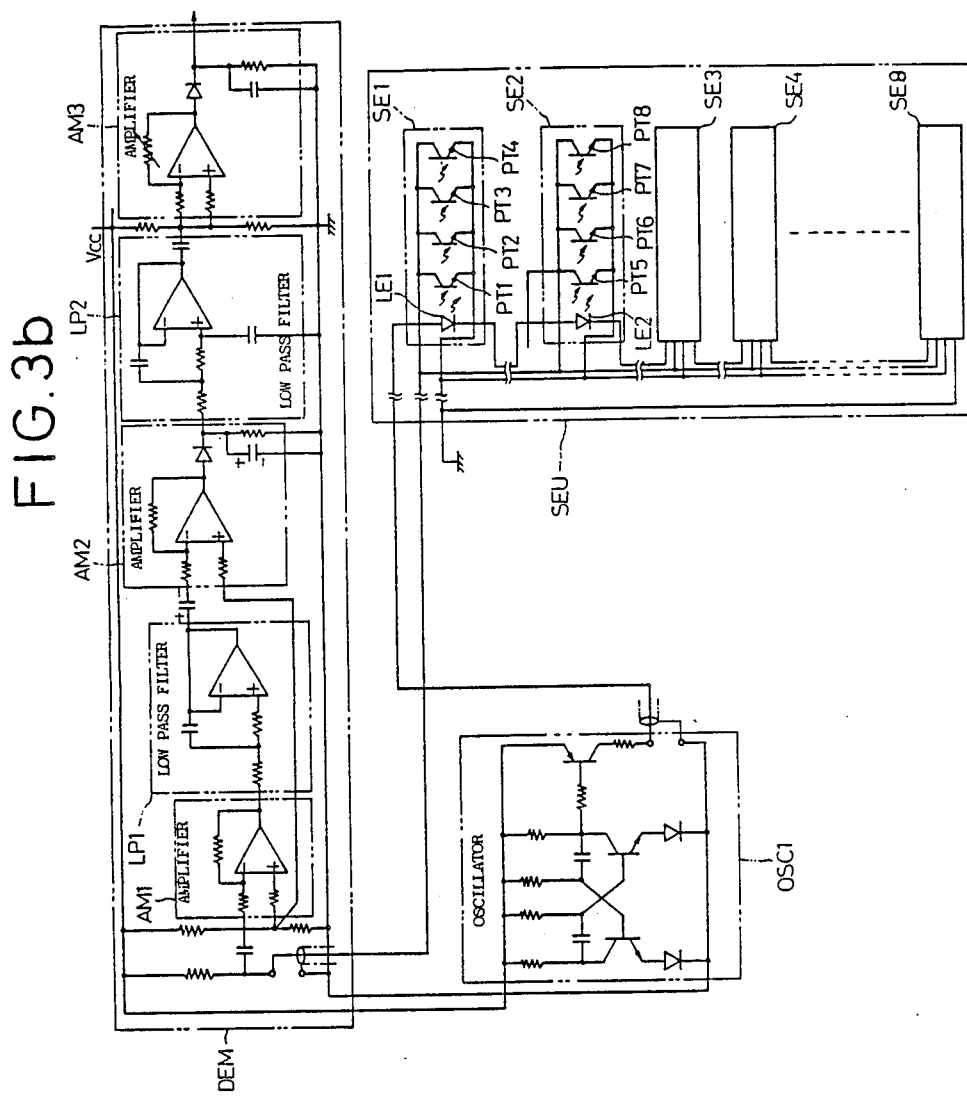

The oscillation circuit OSC1, sensor unit SEU and the demodulation circuit DEM in FIG. 3a are shown in more detail in FIG. 3b. Description will now be made with reference to FIG. 3b. The oscillation circuit OSC1 is of a non-stable multivibrator circuit which is adapted to output a square wave signal of 1 KHz in this example. The sensor unit SEU comprises eight optical sensors SE1-SE8. The light emitting diodes LE1, LE2, . . . of the respective optical sensors SE1-SE8 are connected in series, and the output terminal of the oscillation circuit OSC1 is connected to one end of the former serial circuit.

Accordingly, the light emitting diode of each optical sensor is intermittently lit up with a cycle of 1 msec. When any of the optical sensors SE1-SE8 is positioned to face a human blood vessel, the light reflectance in that part is fluctuated depending on the flow rate of blood, i.e., heartbeat. As a result, an output terminal of the photo transistor in the optical sensor produces an AC signal of 1 KHz modulated in its amplitude in accordance with a heartbeat signal.

The photo transistors PT1, PT2, PT3, . . . of the respective optical sensors SE1-SE8 are connected in parallel, and one end of this parallel circuit is connected to the input terminal of the demodulation circuit DEM. The demodulation circuit DEM is composed of an amplifier AM1, low pass filter LP1, amplifier AM2, low pass filter LP2, amplifier AM3, etc., thereby to demodulate the original heartbeat signal from the 1 KHz signal modulated in its amplitude.

Figure 4:
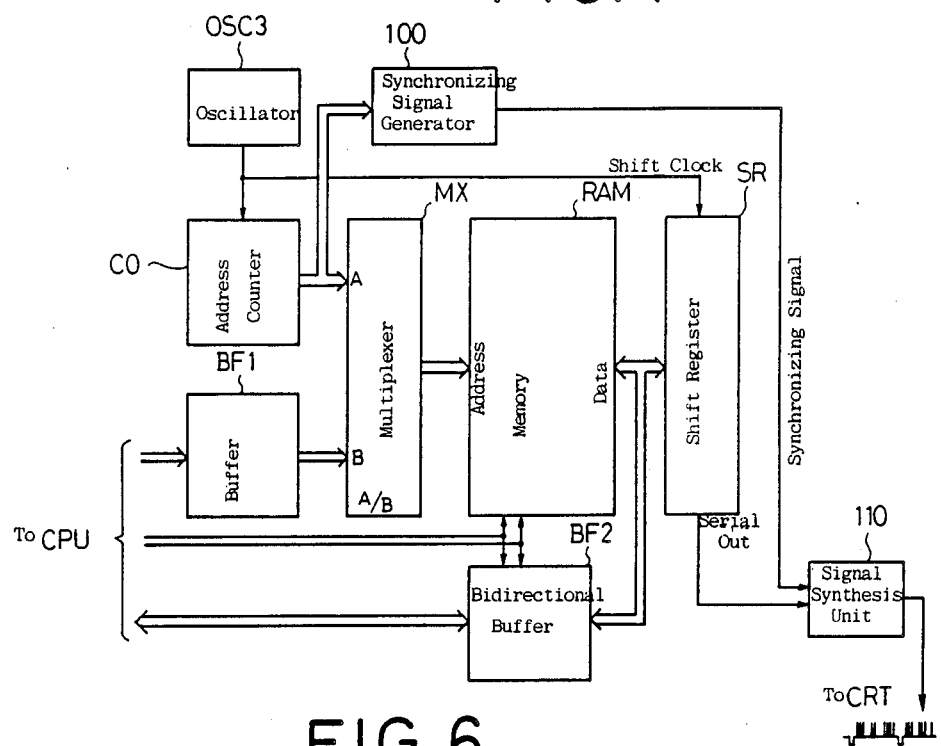

FIG. 4 shows the configuration of the video memory VRAM1 shown in FIG. 3a. It is to be noted that the video memory VRAM2 has the same configuration of the VRAM1. Description will now be made with reference to FIG. 4. A memory RAM stores therein bright-/dark data corresponding to individual picture elements to be displayed on the screen of the Brown tube. Address lines of the memory RAM are connected to a multiplexer MX, thereby selecting the memory address corresponding to either one of the counted value of an address counter CO or the output address from the CPU which are applied to inputs A and B of the MX, respectively.

Such selection is effected by the microcomputer CPU, and in case data is written into or read from the memory RAM, the input B of the MX is designated and the CPU designates the address. In case other than the above, the address of the memory RAM is designated by the counted value of the address counter CO. The address counter CO makes always counting with pulse signals corresponding to the number of picture elements and led from the oscillator OSC3. Connected to an output terminal of the address counter CO is a synchronizing signal generation circuit 100 which is adapted to generate both a vertical synchronizing signal and a horizontal synchronizing signal at the given timing in accordance with the counted value of the CO.

A shift register SR is connected to plural-bit data lines of the memory RAM, and a serial output terminal of the SR is connected to a signal synthesis circuit 110. Also connected to those data lines are data lines of the CPU through a bidirectional buffer BF2.

In case of displaying the given picture elements cn the Brown tube's screen brighter, the CPU writes the data with given bits set equal to "1" into those memories of the RAM which have the addresses corresponding to such picture elements. In this case, the B input of the multiplexer MX is designated, the CPU side and the RAM side of the bidirectional buffer BF2 are respectively designated to be input and output, the given data is set in the address lines and data lines of the CPU, and then a write designating signal is applied to the memory RAM. After completion of the above, the input A of the MX is designated and the RAM side of the bidirectional buffer BF2 is set to become high impedance, until next writing is to be executed.

In such a state, a synchronizing signal is generated for every given timing and the address of the RAM is selected in order correspondingly. When the given address into which the display data is to be written is designated, the plural-bit data including the picture element data is set into the shift register SR, and the data indicating the given "bright" picture element (white picture element) is applied to the signal synthesis circuit 110 with a time lag of given clocks corresponding to the position of the picture element. In this way, the serial data corresponding to the data of all picture elements on the display screen is continuously output, so that this image data and the synchronizing signal are synthesized in the circuit 110 to provide a composite signal, which is then applied to the Brown tube display unit (monitor TV).

Figure 5:
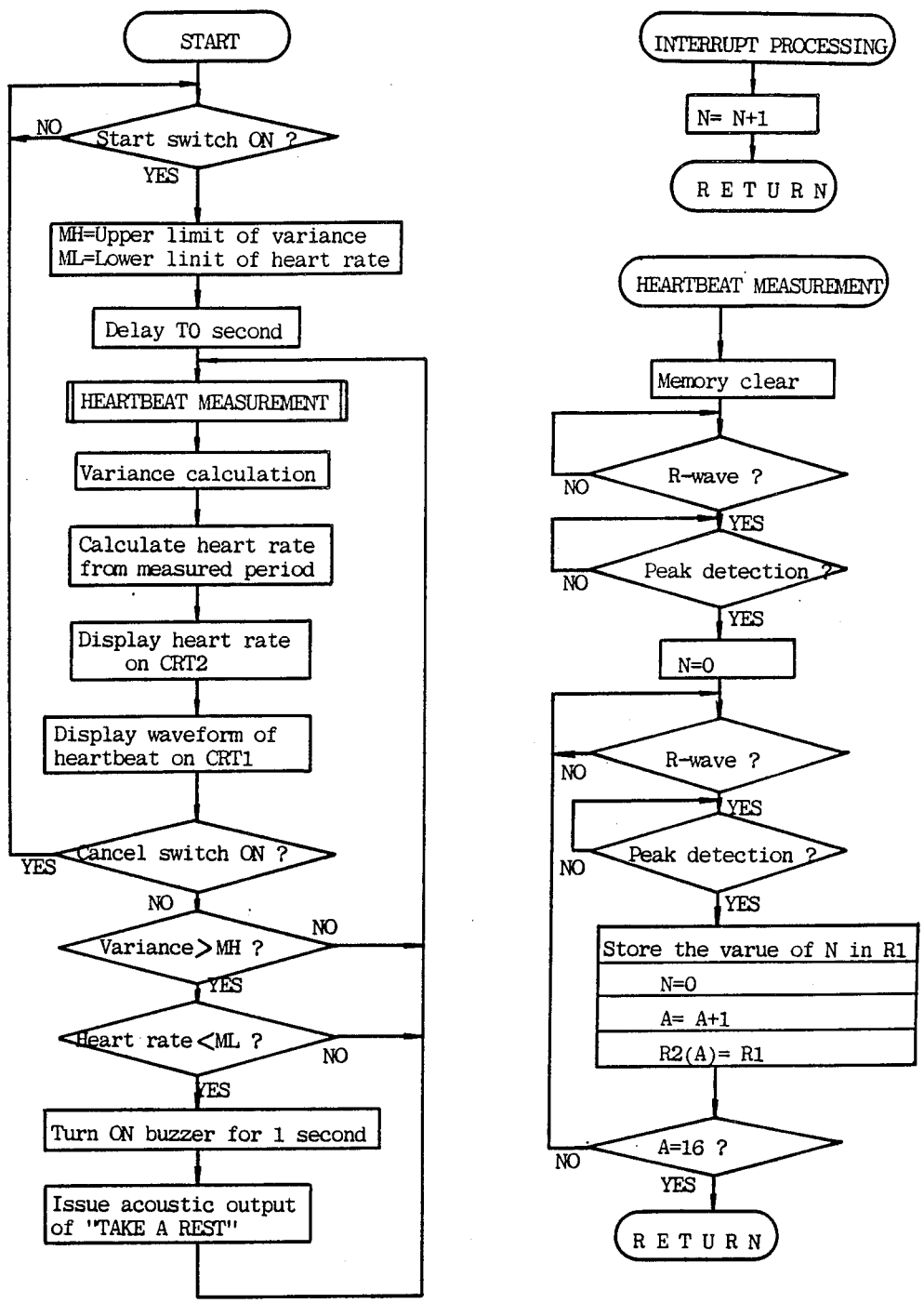

FIG. 5 schematically shows operation of the microcomputer CPU in FIG. 3a. The operation will now be described with reference to FIG. 5.

Interrupt processing is first described. Since a signal from an oscillation circuit OSC2 is applied to an interrupt input terminal INT of the CPU, the CPU implements interrupt processing with a given interval of time. In this interrupt processing, the content of a register N is incremented by +1. More specifically, since the content of the register N is changed in accordance with the lapsed time, if the content of N is cleared to 0 at some timing, the lapsed time from clearing can be known by checking the value of the register N in the main routine. The main routine, subroutines, etc. determine various processing timings by checking the value of the register N.

Next, the main routine will be described. When powered on, the start switch SW1 is first checked. If the start switch SW1 is turned on, voltages set by the variable resistors VR1 and VR2 are converted to digital signals through the A/D converter ADC, and the converted data are stored in the registers MH and ML, respectively. The data in the registers MH and ML respectively exhibit the upper limit value of fluctuations in heartbeat period and the lower limit value of heart rate, which are both used to decide whether or not an alarm is to be issued.

In the following Table 1 there is outlined the relationship between the general average value of heart rate 1/L as well as fluctuations (or variance) in heartbeat period ΔL and the human physical and mental conditions.

TABLE 1

| Human condition | 1/L | ΔL |
| --- | --- | --- |
| In relaxation | small | large |
| In strain | large | small |
| In physical relaxation and in mental strain | small | small |
| In sleeping | small | extremely large |

In general, when driving a road-vehicle, the driver is relaxed physically, but in strain mentally. However, in the event of driving asleep from fatigue or other reasons, the mentally strained condition is eliminated and the heartbeat comes into the state similarly to that in sleeping. In other words, referring to Table 1, in the event the driver falls into a doze while driving a road-vehicle, fluctuations in heartbeat period are rapidly increased.

In this embodiment, therefore, the reference value (upper limit value) MH for fluctuations in heartbeat period and the reference value (lower limit value) ML for heart rate are set to issue an alarm in case the fluctuations are large and the heart rate is less than a predetermined value. Subsequent to setting of both MH and ML, measurement of a heartbeat is started after waiting for that a predetermined time To necessary for stabilizing the detected signal has lapsed. A subroutine for the heartbeat measurement will be described later in detail. After completion of the heartbeat measurement, variance or fluctuations in heartbeat period ΔL are calculated based on the measured result. Assuming that the heartbeat periods of given samples (16 in this example) are given by S, the variance can be determined from the following equation:

$$\text{Variance} = \text{Average value of } S^2 - (\text{Average value of } S)^2$$

Thereafter, heart rate, i.e., the number of heartbeats computed in units of one minute, is calculated from the average value of S. In accordance with the result thus calculated, the corresponding numerical display data previously stored in a ROM (read only memory) within the CPU is read out and then set in the corresponding address of the video memory VRAM2. With this, the numerical value of heart rate is displayed on the Brown tube display unit CRT2 as shown in FIG. 3a by way of example.

Next, the heartbeat signal is sampled by the A/D converter ADC at given times and given intervals, and the sampled data is displayed on the Brown tube display unit CRT1 in the shape of a waveform. It is to be noted that, before making display, the memory RAM should be cleared in advance. Such display processing is performed as follows.

Figure 6:
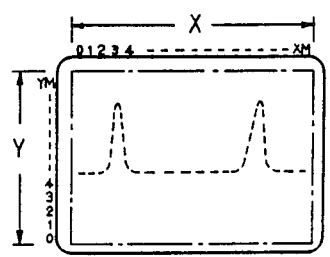
FIG. 6 is a plan view showing an indication on the screen of a display unit CRT.

As shown in FIG. 6, a picture element on the display screen is designated by coordinates (X, Y) in both X- and Y-directions, and the given plot subroutine (not shown) is implemented to set "1" at the given bit in the given address of the memory RAM. Voltage 0 V is assigned to the given Y-coordinate value (e.g., 10), and the designated Y-coordinate value is varied in accordance with the value of the sampled data. For example, when the Y-coordinate value is increased by +1 for every rise of 0.1 V in voltage, the designated Y-coordinate value becomes 25 (10+15) if the sampled voltage exhibits 1.5 V. The X-coordinate value is incremented by +1 for each sampling with the initial value being set equal to 0. Stated differently, in this display processing, the picture elements in the Y-axis corresponding to the sampled voltages are displayed brighter sequentially in the direction from left to right on the screen. Such display processing is continued until the X-coordinate value reaches the rightmost end (i.e., X=XM). As a result, the heartbeat waveform as shown in FIG. 6 is displayed on the display unit CRT1.

Subsequently, whether or not the cancel switch SW2 is turned on is checked, and the CPU proceeds to the following processing if it is turned on. In case the variance ΔL is larger than the content of the register MH and the heart rate 1/L is smaller than the content of the register ML, this means high possibility of driving asleep. From this reason, the buzzer BZ is actuated for one second and the voice synthesis unit VGU is instructed to provide such a voice output as "Take a rest" through the speaker SP. In case the above two conditions are not satisfied simultaneously, there are displayed only the heart rate and the waveform of a heartbeat.

A subroutine for heartbeat measurement will now be described. It is to be noted that registers A, R1 and a plurality of registers R2( ), which are specified by the content of the parenthesis ( ), are employed in this subroutine.

The memories (registers) are first cleared, and the heartbeat signal is sampled by the ADC with a time interval of 2 msec. It is checked whether or not the R-wave has arrived, and if so, it is then checked whether or not there is a peak of the signal.

The term of the R-wave herein means a large mountain-like portion of the heartbeat signal. In this embodiment, it is checked whether or not the differential value, i.e., change in the data for each sampling, is larger than a predetermined value, and the presence of the R-wave is decided when the larger differential value has been resulted continuously given times. Further, in this emboidment, the presence of a peak is decided when a change in the sampling value has been equal to or less than zero continuously two times.

Upon detecting a peak, the content of a counter N (timer) is cleared to zero and a time period (L) from the current peak detection to the next one is measured. This time period represents a so-called R-R interval (or heartbeat period). For each measurement the content of the register A is counted up, and the measured result is stored in the register R2(A). When there is obtained the data corresponding to 16 waves (or A=16), measurement is ended. Thus, the period data corresponding to 16 periods is stored in 16 registers of the register R2(A). Accordingly, the data of variance value and heart rate can be resulted through the above mentioned processing based on the content of the register R2(A).

Although in the above embodiment there are used two Brown tube display units, one of which displays the waveform of a heartbeat and the other of which displays heart rate, it is alternatively possible that a plurality of 7-segment indicators for display of numerical values are provided to display heart rate, that the waveform and heart rate are both displayed on a single two-dimensional indicator for displaying the waveform of a heartbeat in a superimposed relation, or that the waveform and heart rate are selectively displayed by turning over a switch or at a certain period.

Although in the above embodiment the light emitting and receiving elements are directly mounted on the peripheral wheel portion of the steering wheel, it is also possible, for example, that light emitting and receiving elements are provided in a body of the electric circuit at the center of the steering wheel and optical fibers are used to guide beams of light. Use of optical fibers permits a reduction in the number of light emitting and receiving elements, because a plurality of optical fibers can be connected to the light emitting surface of one light emitting diode or the light receiving surface of one photo transistor. It is to be noted that, since an optical fiber is not susceptible to bend at a right angle in a small space, a mirror or the like is required to make the optical axis turn toward above the steering wheel as shown in the above embodiment.

Figure 7A:
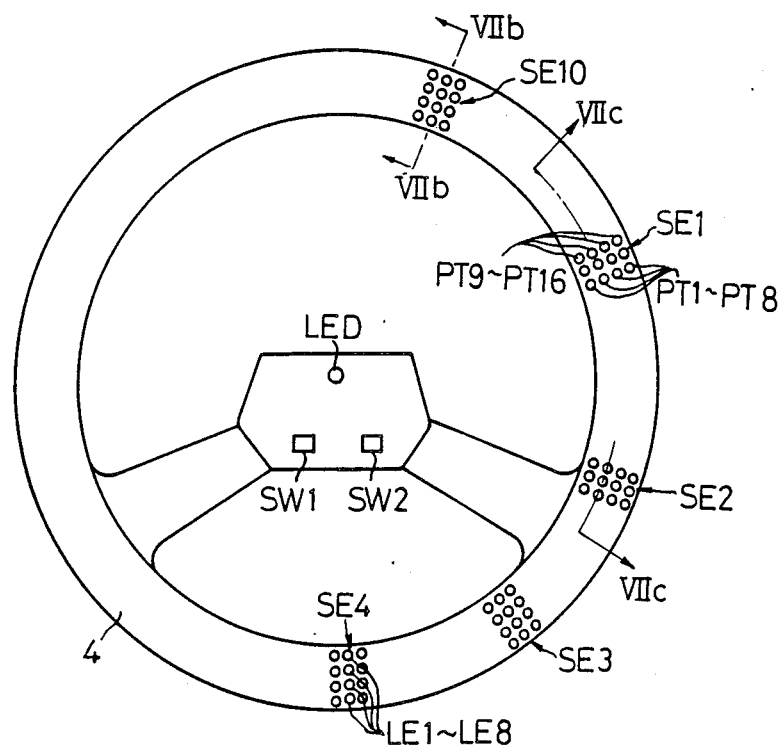
FIG. 7a is a plan view showing a steering wheel according to a modified embodiment.
Figure 7B:
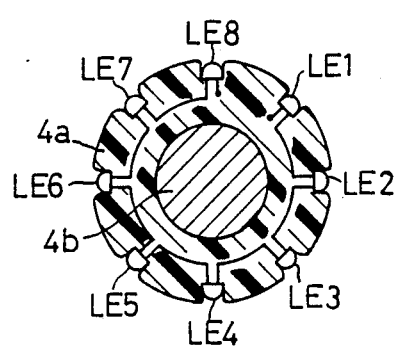
Figure 7C:
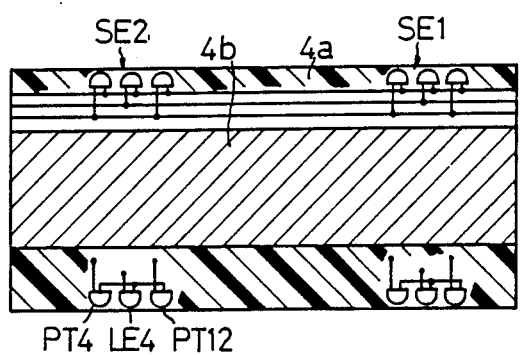
Figure 7D:
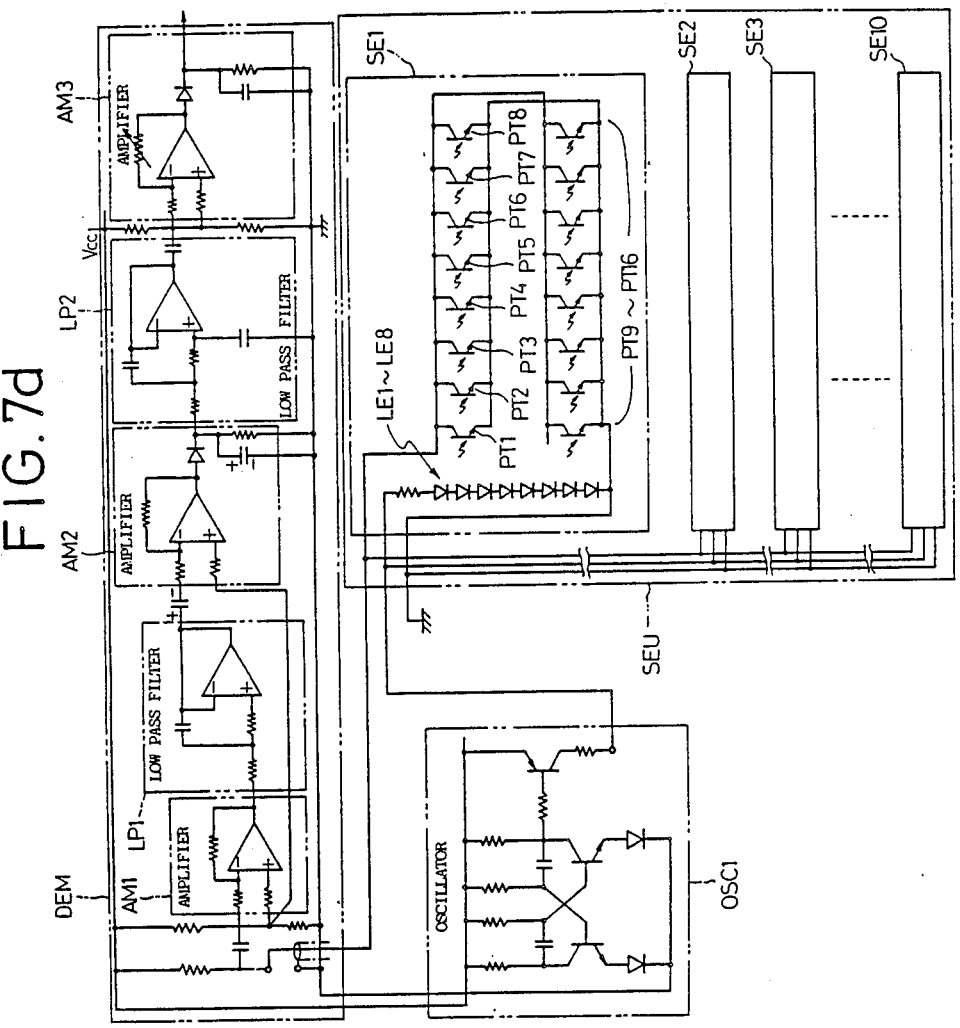

Hereinafter, there will be described one modified embodiment relating to arrangement of the optical sensors. FIGS. 7a, 7b and 7c show a steering wheel in the modified embodiment, and FIG. 7d shows a part of an electric circuit. Referring to these figures, reflection type optical sensors SE1, SE2, . . . , SE10 are arranged in the peripheral wheel portion of a steering wheel 4 in a dispersed relation to one another. Each optical sensor comprises 8 light emitting diodes LE1–LE8 arranged into the annular form interlinking with the steering wheel, and 16 photo transistors (PT1–PT16) so arranged that every pair of two photo transistors are located to sandwich each light emitting diode. The light emitting diodes equipped in each optical sensor are formed of infrared light emitting diodes which emit a beam of light in an infrared range. One light emitting diode and two photo transistors of each optical sensor in a corresponding positional relation are arranged to have their optical axes extending in the same direction (i.e., in the direction perpendicular to the mounted surface). The steering wheel 4 is composed of an iron core 4b and a resin 4a covering the former, and the respective optical sensors are secured to the portion of the resin 4a. Electric wires led from each optical sensor are connected to an electronic circuit housed in a panel at the center of the steering wheel 4 after passing through the inside of the resin 4a.

Still another embodiment of the present invention will now be described. In this embodiment, a large number of optical sensor sets are arranged on a steering wheel, and only those optical sensors which produce a given signal are selectively used to perform the heartbeat measurement.

Figure 8A:
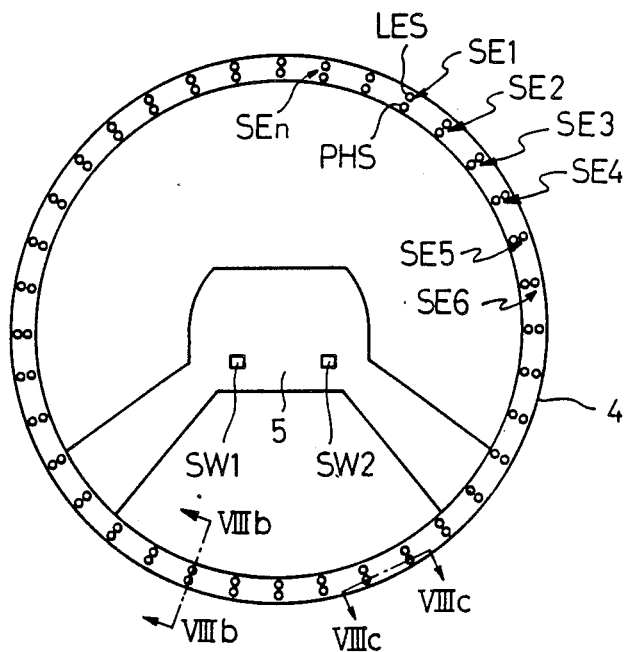
FIG. 8a is a plan view showing a steering wheel according to still another embodiment.
Figure 8B:
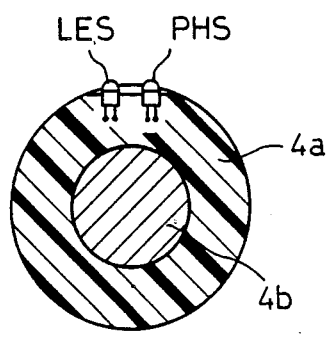
Figure 8C:
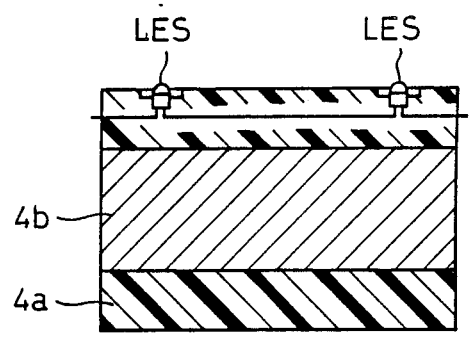

A steering wheel 4 is shown in FIGS. 8a, 8b and 8c. Referring to these figures, a number of reflection type optical sensors SE1, SE2, ..., SEn are dispersedly arranged on the upper surface of the steering wheel 4 with given intervals (each interval smaller than at least a width of the hand). Each optical sensor comprises a light emitting diode LES and a photo transistor PTS positioned near the former. The light emitting diode equipped in each optical sensor is formed of an infrared light emitting diode which emits a beam of light in an infrared range. The light emitting diode LES and the photo transistor PTS in each optical sensor are arranged to have their optical axes extending in the same direction (toward above the steering wheel 4). The steering wheel 4 comprises an iron core 4b and a resin 4a covering the former, and the respective optical sensors are fixedly buried in the portion of the resin 4a leaving their light emitting and receiving portions to face the outside. Electric wires led from each optical sensor are connected to an electronic circuit housed in a panel at the center of the steering wheel 4 after passing through the inside of the resin 4a.

Figure 9A:
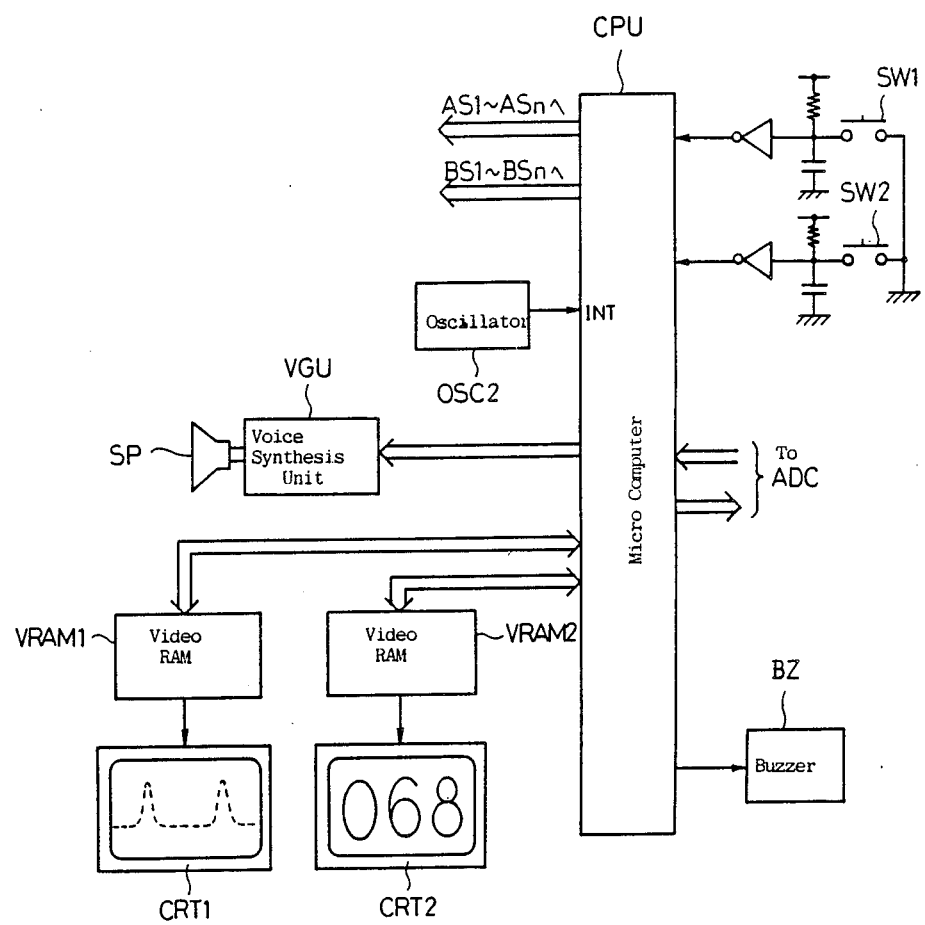
Figure 9B:
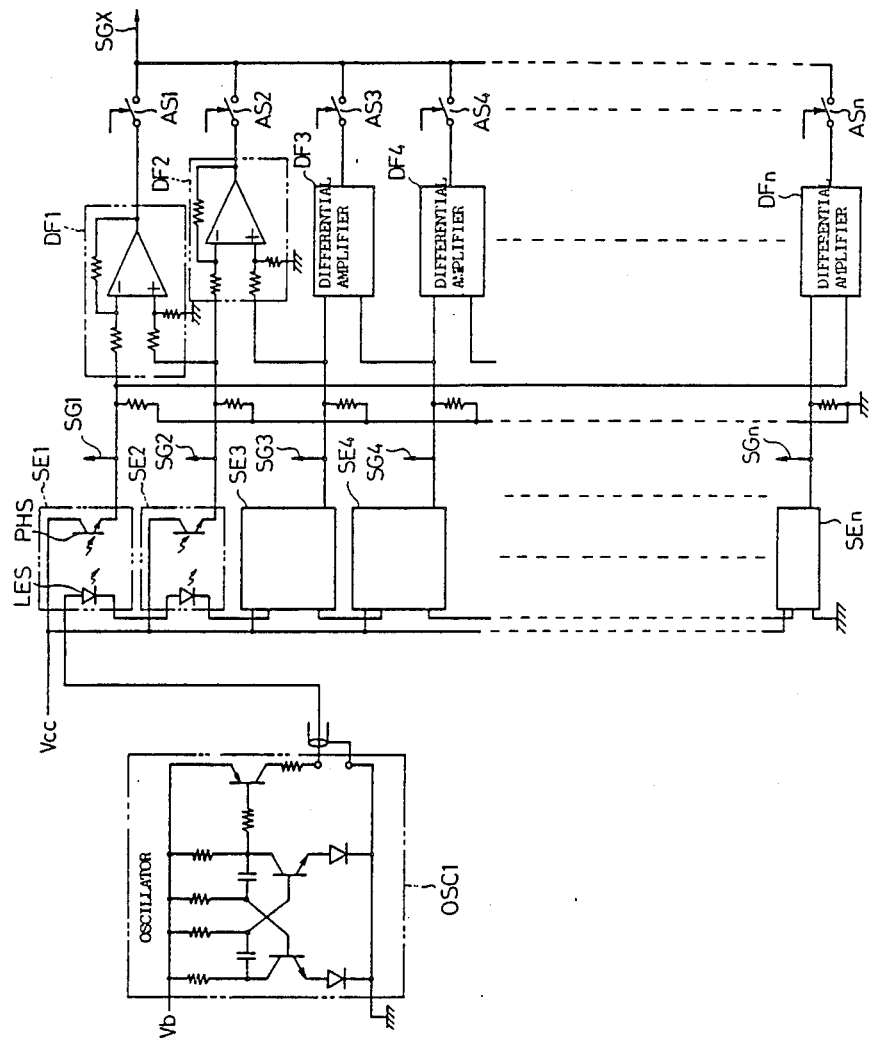
Figure 9C:
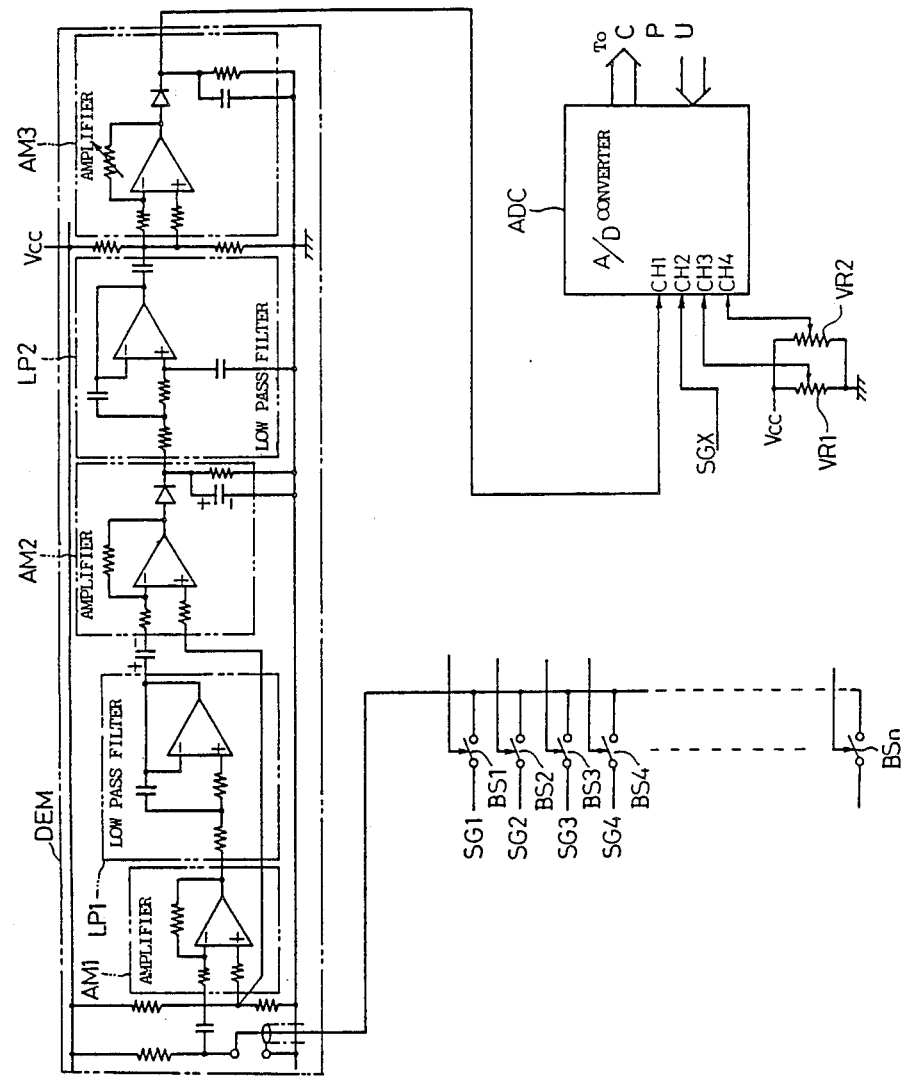

FIGS. 9a, 9b and 9c show the configuration of an electronic circuit of the heartbeat meter loaded on road-vehicles. It is a microcomputer CPU that controls the entire circuit. In this embodiment, connected to the microcomputer CPU are a voice synthesis unit VGU, buzzer BZ, video memories VRAM1 and VRAM2, analog/digital converter ADC, etc. A speaker SP is connected to an output terminal of the voice synthesis unit VGU, and Brown tube display units CRT1, CRT2 are connected to output terminals of the video memories VRAM1, VRAM2, respectively. An oscillation circuit OSC2 connected to an interrupt input terminal INT of the microcomputer CPU periodically issues an interrupt request to the CPU with a relatively short period. The start switch SW1 and the cancel switch SW2 are connected to input ports of the CPU through respective inverters, etc.

Referring now to FIG. 9b, the light emitting diodes LES equipped in the optical sensors SE1-SEn are connected in series, one end of which serial circuit is connected to an oscillation circuit OSC1 and the other of which is grounded. In this embodiment, the oscillation circuit OSC1 oscillates the frequency of 1 KHz and generates voltage in the square wafeform. But a lower level of the voltage is not equal to zero. Therefore, the intensity of light emitted from the light emitting diode LES of each optical sensor is varied in a binary fashion with a period of 1 msec. When any of the optical sensors SW1-SEn is positioned to face a human blood vessel, the light reflectance in that part of the blood vessel is fluctuated depending on an amount of blood flow rate, i.e., heartbeat, so that an output terminal of the photo transistor in each optical sensor produces an AC signal of 1 KHz modulated in its amplitude in accordance with the heartbeat signal.

Differential amplifiers DF1-DFn are connected to output terminals of the optical sensors SE1-SEn. The respective differential amplifiers are connected so as to amplify the potential difference between every adjacent optical sensors. More specifically, an output line SG1 of the optical sensor SE1 is connected to one input terminal of the differential amplifier DF1, while an output line SG2 of the optical sensor SE2 adjacent to the former in the clockwise direction is connected to the other input terminal of the differential amplifier DF1. Other differential amplifiers DF2-DFn are connected similarly.

Respective output lines of the differential amplifiers DF1-DFn are commonly connected through corresponding analog switches AS1-ASn to form a signal line SGX, which is connected to one input terminal CH2 of the analog/digital converter ADC. Control input terminals of the individual analog switches AS1-ASn are connected to corresponding different output ports of the microcomputer CPU, respectively.

The output lines SG1-SGn of the optical sensors SE1-SEn are commonly connected through respective analog switches BS1-BSn to form a single signal line, which is connected to an input terminal of a demodulator DEM. Control input terminals of the analog switches BS1-BSn are connected to the corresponding different output ports of the microcomputer CPU, respectively. The demodulator DEM is composed of an amplifier AM1, low pass filter LP1, amplifier AM2, low pass filter LP2, amplifier AM3, etc., thereby demodulating the original heartbeat signal from the 1 KHz signal modulated in its amplitude. An output terminal of the demodulator DEM is connected to one input terminal CH1 of the analog/digital converter ADC. Connected to other input terminals CH3 and CH4 of the analog/digital converter ADC are variable resistors VR1 and VR2 for setting the upper and lower limit values of variance (fluctuations) in heartbeat period, respectively.

Figure 10A:
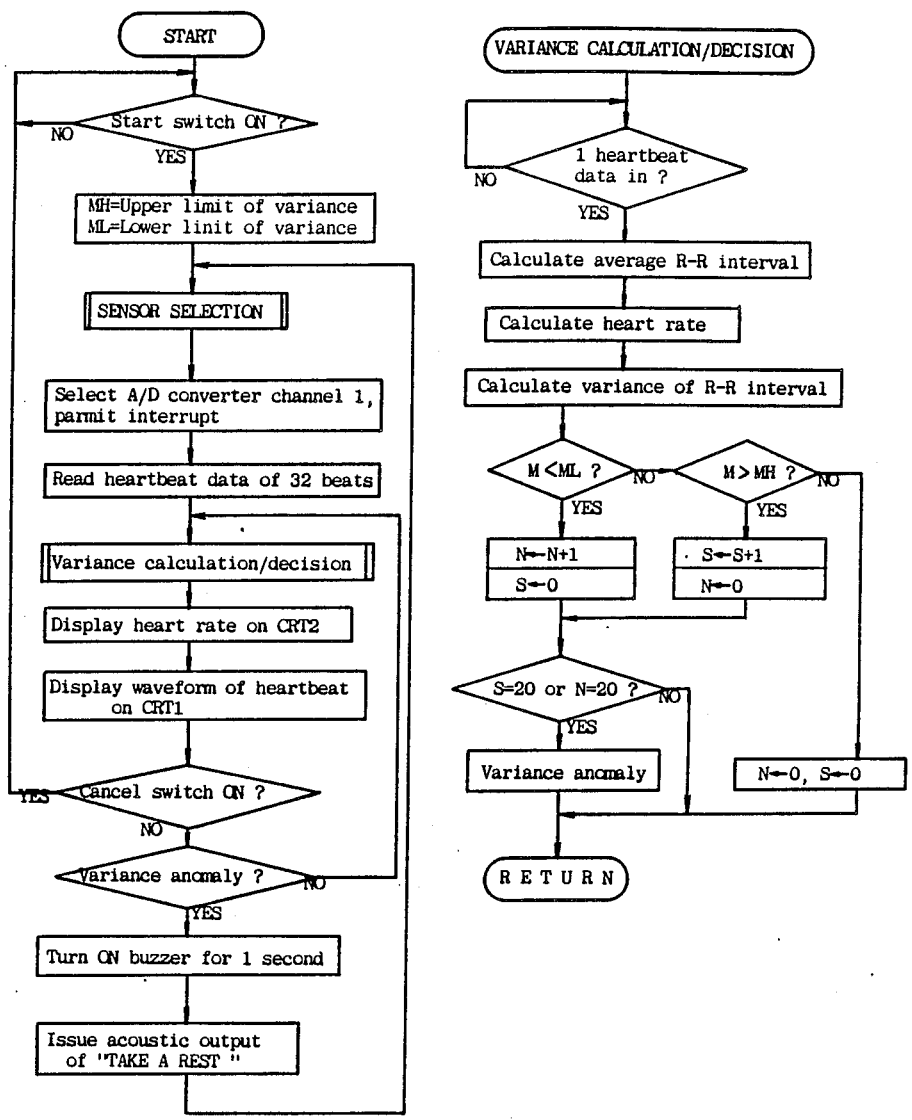
Figure 10B:
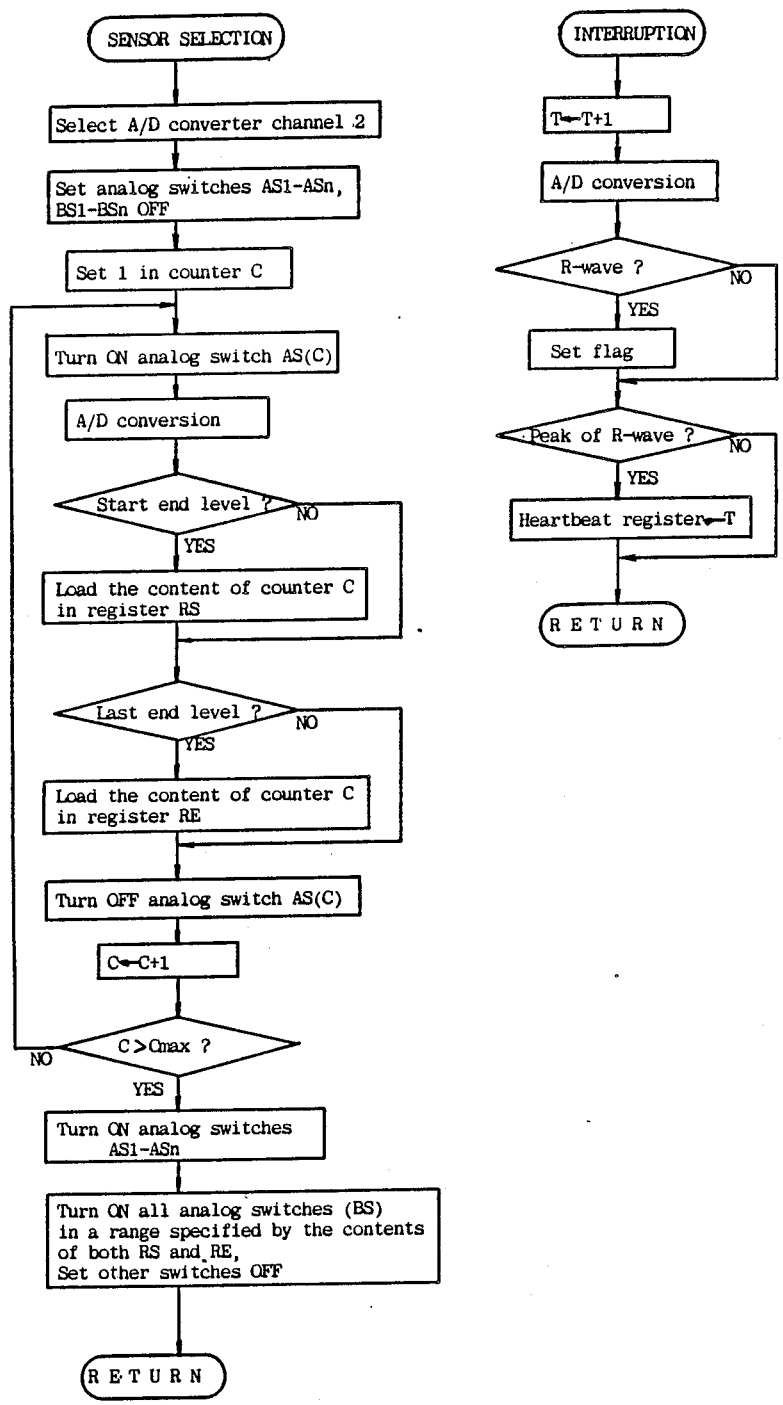

FIGS. 10a and 10b schematically show operation of the microcomputer CPU shown in FIG. 9a. Description will now be made with reference to FIGS. 10a and 10b. When the start switch SW1 is turned on, the CPU first reads the preset values of the variable resistors VR1 and VR2 through the analog/digital converter ADC, these preset values being set as a variance upper limit value MH and a raviance lower limit value ML. Thereafter, a sensor selection subroutine is implemented.

In the sensor selection subroutine, the CPU first selects CH2 as an input channel of the analog/digital converter ADC. Subsequently, the analog switches AS1-ASn and Bs1-Bsn are set off and the initial value of 1 is then set in a counter (register) C. The particular analog switch AS(C) determined by the content of the counter C is turned on, and an output of the analog/digital converter ADC is read. In other words, since a signal level of the signal line SGX is read in this case, the CPU reads the difference in output level between the optical sensors SE1 and SE2 if the counter C assumes 1.

Figure 11A:
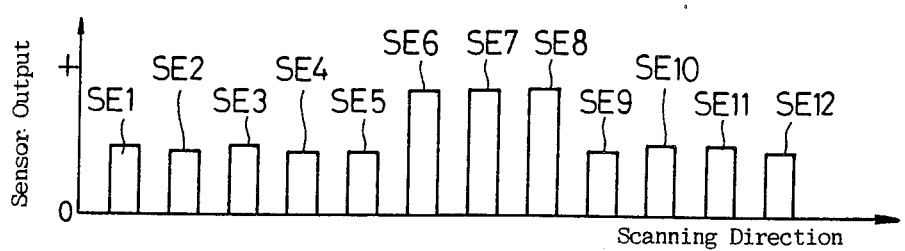
Figure 11B:
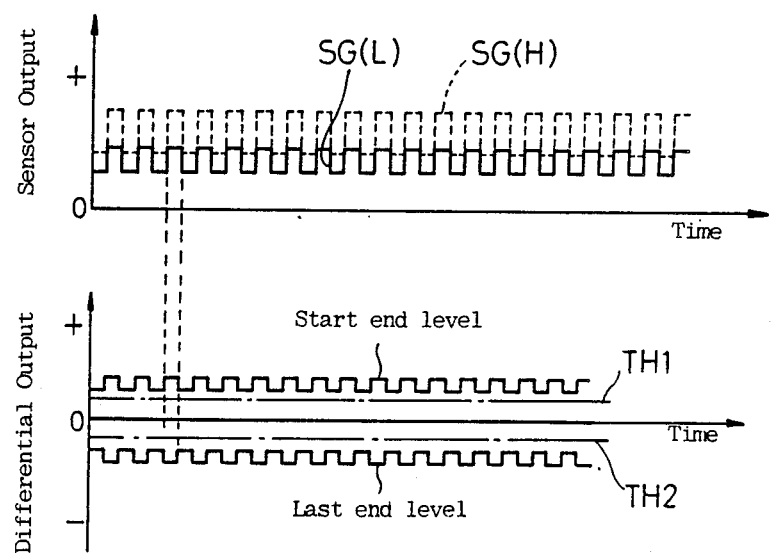
FIG. 11b is a timing chart showing an output signal level of one optical sensor and the waveform of an output from a differential amplifier.

Assuming now, for example, that the driver grips the part of the steering wheel corresponding to the optical sensors SE6, SE7 and SE8, the respective sensors produce their output levels as shown in FIG. 11a. More specifically, the optical sensors SE6-SE8 in the part where the driver's hand is placed produce output levels higher than those produced by the remaining optical sensors SE1-SE5 and SE9-SEn. The difference in output level between the adjacent optical sensors is compared with two threshold levels TH1 and TH2 as shown in FIG. 11b to discriminate the following three states; both output levels are equal to each other, one level is higher than the other level by a given or more amount, and one level is lower than the other level by a given or more amount. Thus, in case the value of the counter C is equal to 5, the output level of the differential amplifier DF5 exhibits a given plus level (higher than TH1), and in case the value of the counter C is equal to 8, the output level of the differential amplifier DF8 exhibits a given minus level (lower than TH2). In other cases, all the remaining differential amplifiers exhibit their output levels between TH1 and TH2.

With the given plus level being defined as a start end detection level and the given minus level being defined as a last end detection level, since the heartbeat signal is obtained from the optical sensors SE6–SE8, outputs of all those optical sensors (SE6–SE8 in this case) are selected which are specified by the values from the content of the counter C plus one at the time when the start end detection level is obtained to the content of the counter C at the time when the last end detection level is obtained, thus resulting in the heartbeat signal of high S/N ratio.

In this embodiment, the content of the counter is changed from 1 to Cmax or n to scan the output levels of the differential amplifiers DF1–DFn, and the content of the counter C at the time when the start end detection level is obtained is stored in a start end register RS, while the content of the counter C at the time when the last end detection level is obtained is stored in a last end register RE. After completion of scanning, the contents of the registers RS and RE are checked and the corresponding analog switches (BS) are set on so as to select those optical sensors between the checked two contents. In other words, the analog switches BS6, BS7 and BS8 are set on in this embodiment.

Therefore, applied to the input terminal of the demodulator DEM is the sum of signals output from only those optical sensors which is actually producing the heartbeat signal. Upon completion of the sensor selection subroutine, the CPU sets CH1 as an input channel of the analog/digital converter ADC to permit interruption. Once interruption is permitted, an interrupt request is applied to the microcomputer CPU for each period of the signal output from the oscillation circuit OSC2, so that the CPU executes interrupt processing. In the interrupt processing, the content of a register T used as a timer is incremented by +1, and an input level of the analog/digital converter is read through A/D conversion. The signal level thus read is checked to decide whether or not the R-wave has been detected, or whether or not a peak of the R-wave has been detected. In case of detecting the R-wave, a given flag is set, and in case of detecting a peak of the R-wave, the content of the register T is stored into a given heartbeat register and both the flag and the register T are cleared.

The term of the R-wave herein means a waveform component corresponding to the large mountain-like portion contained in the heartbeat signal. In this embodiment, it is checked whether or not the differential value, i.e., level change for each sampling, is larger than a predetermined value, and the presence of the R-wave is decided when the larger differential value has been resulted continuously given times. Further, in this embodiment, the presence of a peak is decided when a change in the signal level sampled after detection of the R-wave has been equal to or less than zero continuously two times.

The content of a register T is cleared every when detecting a peak of the R-wave, so the content of the register T immediately after detection of a peak corresponds to the time lapsed between a peak of the previous R-wave and a peak of the current R-wave, that is, a period of the R-wave (R - R interval).

In the main routine, the CPU proceeds to the next variance calculation/decision subroutine after waiting for that the haertbeat data corresponding to 32 beats has been stored by the interrupt processing. In the variance calculation/decision subroutine, after waiting for storage of the heartbeat data corresponding to one beat, the new heartbeat data and the previous 31-heartbeat data (the oldest data is erased) are processed as follows. First, the average heartbeat period is obtained by determining the average value of the 32-heartbeat data. Next, an inverse number of the above average value, i.e., heart rate, is determined. Further, fluctuations or variance of the heartbeat period is determined. The variance value M in this case can be determined by the following equation provided that each heartbeat period is represented by S:

Variance M = Average value of $S^2$ - (Average value of $S)^2$. Thereafter, the resulted variance value M is compared with the variance upper limit value MH and the variance lower limit value ML. If M<ML, the register S is cleared and the content of the register N is counted up by +1. If M>MH, the register N is cleared and the content of the register S is counted up by +1. And if MH>M>ML, the contents of both the registers S and N are cleared. When the content of the register N or S reaches 20, a flag indicating a variance anomaly is set.

In other words, the case the variance values for 20 heartbeats have been too large or small continuously, is decided as variance anomaly. The variance calculation/decision subroutine is repeatedly implemented for each sampling of the heartbeat data, until the cancel switch SW2 is depressed or there occurs a variance anomaly. The Brown tube display unit CRT1 displays the waveform of a heartbeat, and the CRT2 displays heart rate. If the flag indicating a variance anomaly is set, it is detected in the main routine, thereby actuating the buzzer BZ for one second and issuing an alarm of "Take a rest" in voice.

In case of judging the difference in output levels between every adjacent sensors as shown in the foregoing embodiment, since an influence of extraneous lights or noises acts on output levels from both sensors similarly even if they are relatively strong, it can be surely decided that which optical sensors from one location to the other location should be utilized for detection of a heartbeat. Although in the above embodiment there are employed the differential amplifiers DF1–DFn, it is alternatively possible that, if a conversion time of the A/D converter and a processing time of the microcomputer CPU are both sufficiently short, the differential amplifiers are omitted, and the CPU reads output levels of all the sensors and then calculates the level difference between the every adjacent sensors. To the contrary, analog comparators may be connected to the output terminals of the differential amplifiers DF1–DFn to decide their output levels, so that the analog switches (BS) may be controlled based on the decided results.

Although in the above embodiment the difference in output level between every adjacent sensors is decided at the time of selecting sensors to eliminate an influence of extraneous lights, such an influence of extraneous lights can be similarly eliminated also by such a construction that output levels of all the sensors are first averaged and the difference between the thus-averaged level and the individual output levels is decided. In this case, the average value may be obtained through calculation or from an output level of an optical sensor provided in such a position as surely providing an average level, e.g., at the center of the steering wheel.

In case an excited amount of the light emitting element (i.e., light emitting diode LES) in each optical sensor is periodically changed as described in the above embodiment, an amplitude of periodical changes produced on the light receiving element suffers no influence of extraneous lights. Accordingly, only the frequency component of a signal output from the oscillation circuit OSC1 may be extracted by a narrow band filter so as to decide its level. Further, if a conversion time of the A/D converter ADC is sufficiently short as compared with a period of the OSC1, it is also possible that an output level of the same sensor is sampled plural times for a short period of time and the sampled results are compared with one another to obtain a desired amplitude.

Furthermore, although in the above embodiment an alarm is used in accordance with the variance value of the heartbeat period, it may be decided in accordance with both the variance value and heart rate whether or not an alarm is to be issued.

In the above embodiment, because the heartbeat detectors are buried in the steering wheel, those detectors can not be detached from the steering wheel. Therefore, another embodiment will now be described in which the heartbeat detectors are fitted to a steering wheel cover.

Figure 12A:
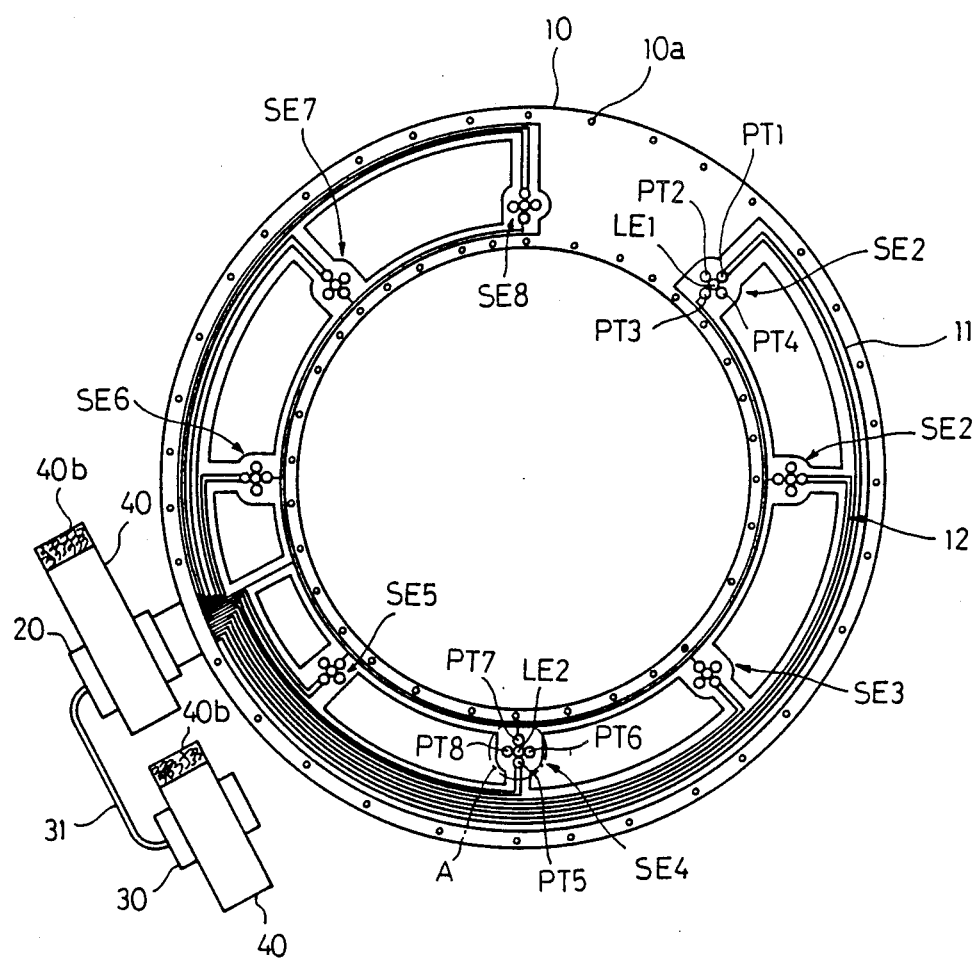
FIG. 12a is a plan view showing a steering wheel cover to which fitted are heartbeat detecting units, according to still another embodiment.
Figure 12B:
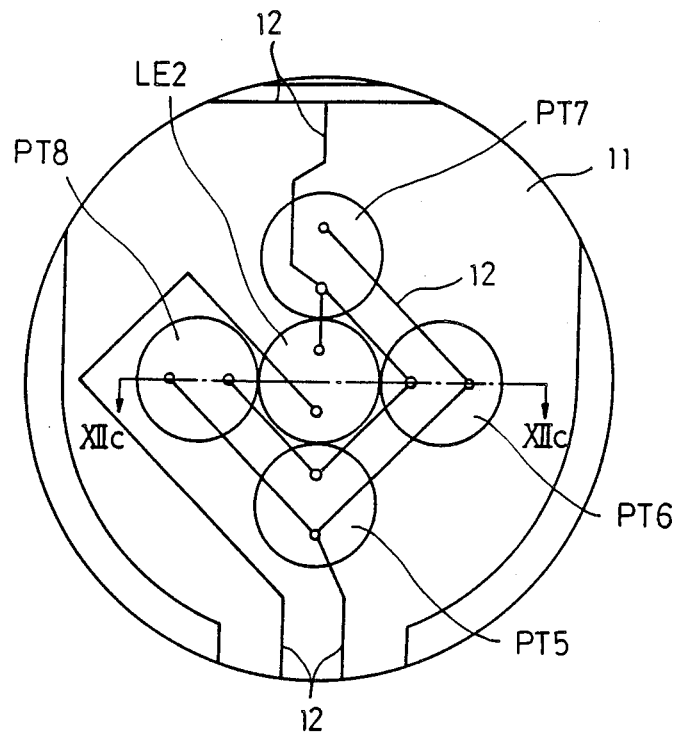
Figure 12C:
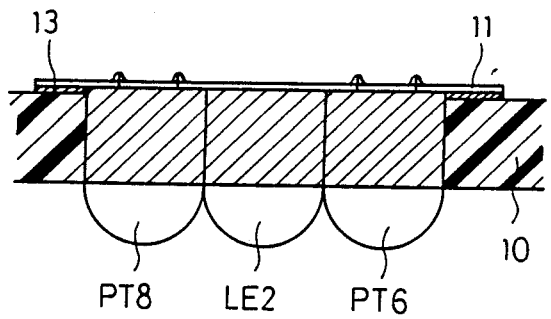
FIG. 12c is a sectional view taken along the line XIIc—XIIc in FIG. 12b.

FIG. 12a shows a steering wheel cover 10, FIG. 12b shows an enlarged view of a part A in FIG. 12a, and FIG. 12c shows a sectional view taken along the line XIIc-XIIc in FIG. 12b. On the rear surface of the steering wheel cover (hereinafter abbrevated to cover) 10, there are dispersedly arranged reflection type optical sensors SE1, SE2, ... SE8. Each of the optical sensors comprises one light emitting diode (LE1) and four photo transistors (PT1-PT4) disposed around the former. The light emitting diode equipped in each optical sensor is formed of an infrared light emitting diode which emits a beam of light in an infrared range. On light emitting diode and four photo transistors in each optical sensor are arranged to have their optical axes extending in the same direction (toward above the steering wheel in the state where the cover is fitted over the steering wheel).

Further, the respective optical sensors are wired through electric wires formed on a flexible substrate 11 (see FIG. 12b). An end of the flexible substrate 11 is connected to a transmitting unit 20 equipped with a light emission actuating means and a signal transmitting means (see FIG. 12a).

A battery box 30 is connected to the transmitting unit 20 through electric wires 31. The transmitting unit 20 and the battery box 30 are separately attached to support members 40, each of which is provided at both ends thereof with downy tapes (or hair-planted tapes) 40a and 40b. It is to be noted that the cover 10 has a number of through holes 10a which are used for fitting it over the steering wheel.

Figure 13A:
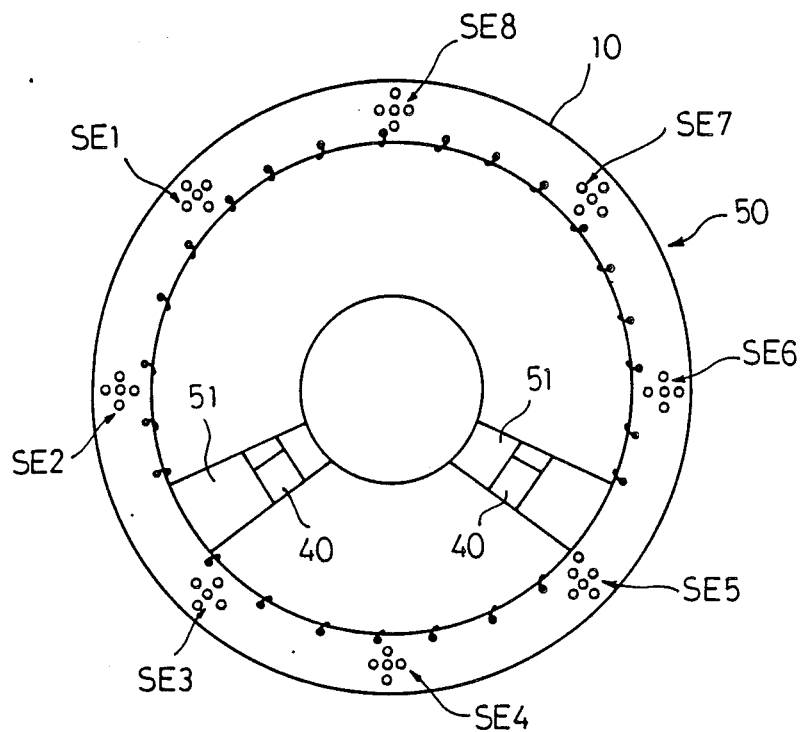
Figure 13B:
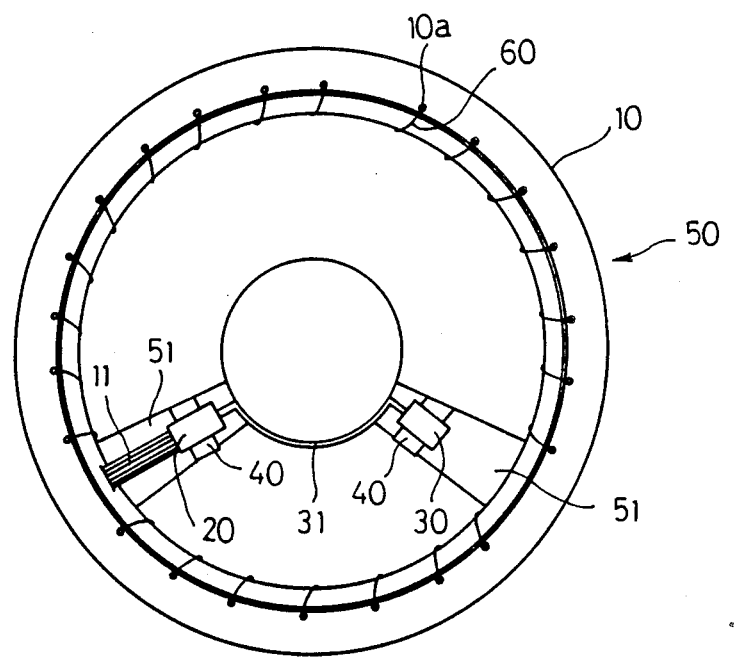

FIGS. 13a and 13b show the state where the cover 10 is fitted over a steering wheel 50. Referring first to FIG. 13a, the cover 10 is fixedly fitted over the steering wheel 50 by the use of a fastening string 60 such that the respective optical sensors SE1-SE8 are positioned on the front side of the steering wheel 50. Referring now to FIG. 13b, on the rear side of the steering wheel 50, the transmitting unit 20 and the battery box 30 are separately attached to the portions of two spokes 51. More specifically, the transmitting unit 20 and the battery box 30 are fixed in such a manner that each of their support members 40 is wound round the corresponding spoke 51, and the downy tapes 40a and 40b arranged at both ends of the support member 40 are bonded to each other.

Figure 14:
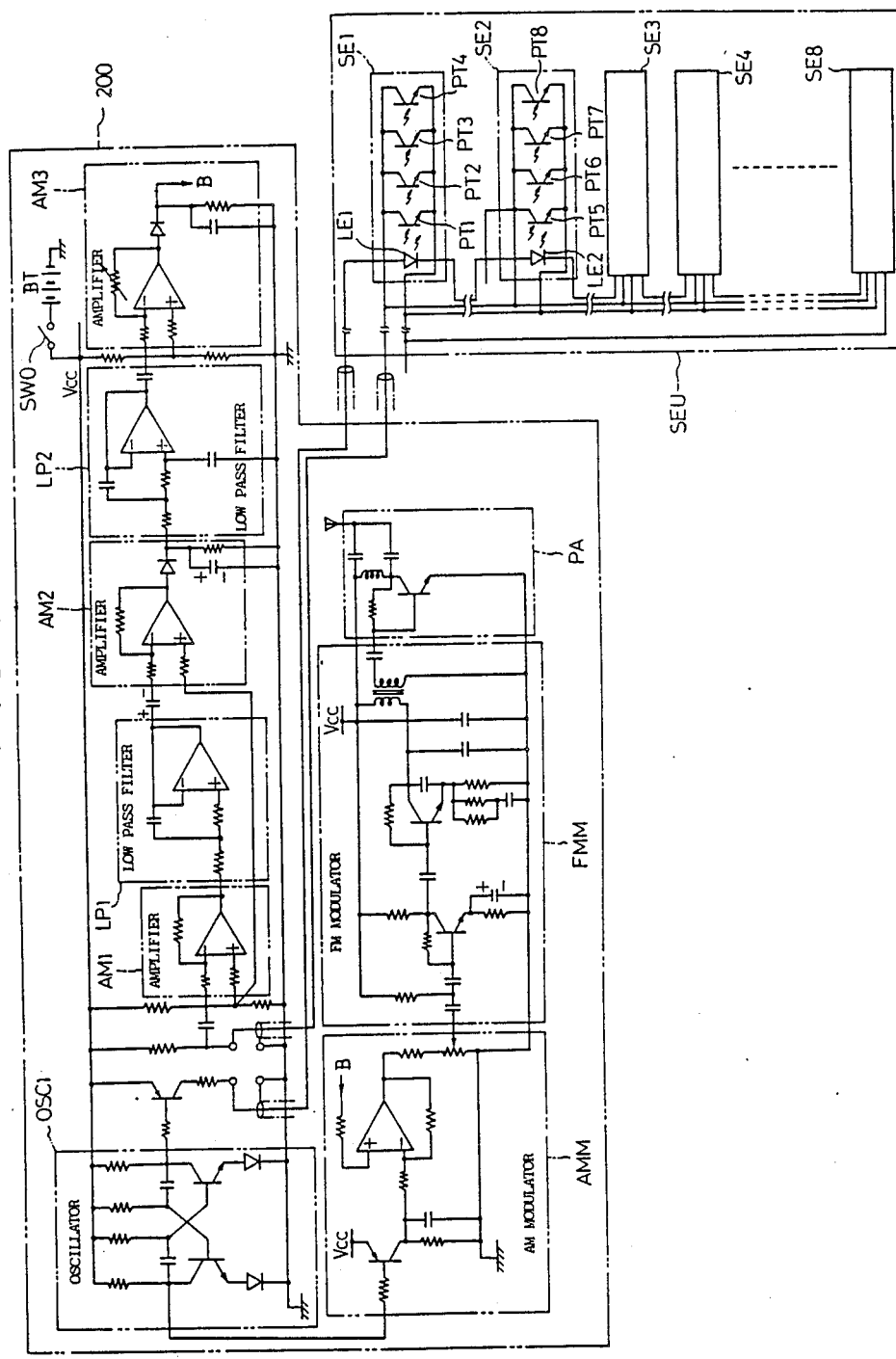
FIG. 14 is an electric circuit diagram showing the heart rate detecting unit shown in FIG. 12a and a transmitting unit connected thereto.
Figure 15:
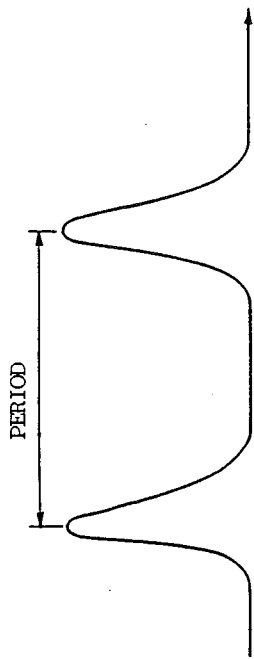
FIG. 15 is a waveform chart showing one example of the heartbeat waveform.

FIG. 14 shows the circuit configuration of an electronic circuit 200 housed in the transmitting unit 20 and a sensor unit SEU. Referring now to FIG. 14, an oscillation circuit OSC1 is formed of a non-stable multivibrator circuit, which outputs a square wave signal of 1 KHz in this embodiment. The sensor unit SEU comprises eight optical sensors SE1-SE8 and their light emitting diodes LE1, LE2, ... are connected in series, to one end of which serial circuit connected is an output terminal of the oscillation circuit OSC1.

Therefore, the light emitting diode of each optical sensor is intermittently lit up with a period of 1 msec. When any of the optical sensors SE1-SE8 is positioned to face a human blood vessel, the light reflectance of that part of the blood vessel is fluctuated depending on an amount of blood flow rate, i.e., heart rate. Accordingly, an output terminal of the photo transistor in the corresponding optical sensor produces an AC signal of 1 KHz modulated in its amplitude in accordance with the heartbeat signal.

Photo transistors PT1, PT2, PT3, ... of the respective optical sensors SE1-SE8 are connected in parallel, and the AC signal produced at one end of such parallel circuit is demodulated to a heartbeat signal through an amplifier AM1, low pass filter LP1, amplifier AM2, low pass filter LP2 and an amplifier AM3. This heartbeat signal is applied to an AM (amplitude modulation) modulator AMM. Applied to one end of the modulator AMM is the signal of 1 KHz from the oscillation circuit OSC1, which signal is converted to a square wave through a filter and then modulated in its amplitude in accordance with a level of the heartbeat signal. An output signal of the modulator AMM passes through an FM (frequency modulation) modulator FMM and a power amplifier PA, and it is then radiated as an electric wave from a transmitting antenna.

Since the heartbeat signal has very low frequency of about 1 Hz, if the signal is directly transmitted while being carried on an electric wave, it is difficult to demodulate the signal on the receiving side. In this embodiment, therefore, the heartbeat signal is first modulated in its amplitude to have relatively high frequency and then subjected to frequency modulation, the resultant signal being carried on an electric wave so as to be transmitted.

Figure 16B:
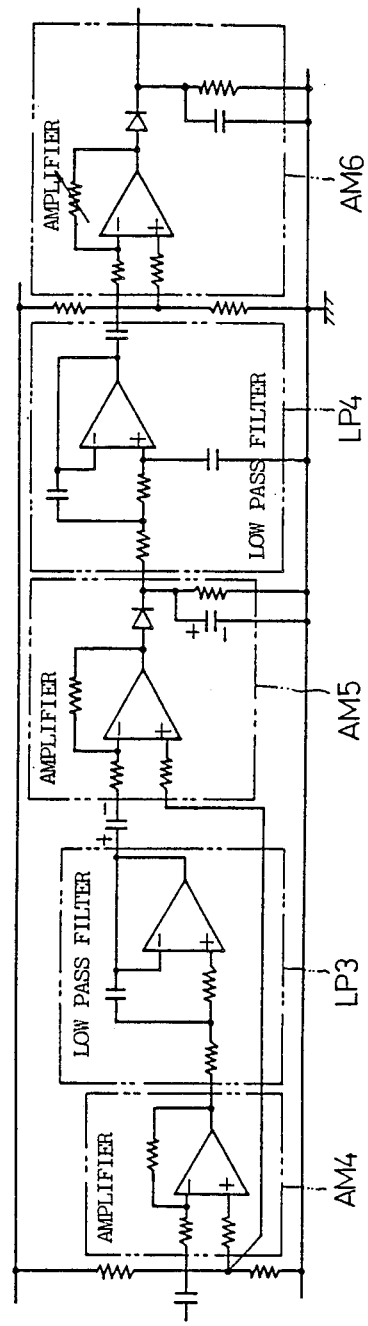
FIGS. 16a and 16b are block diagrams showing an apparatus body for receiving an electric wave emitted from the apparatus shown in FIG. 14.
Figure 16A:
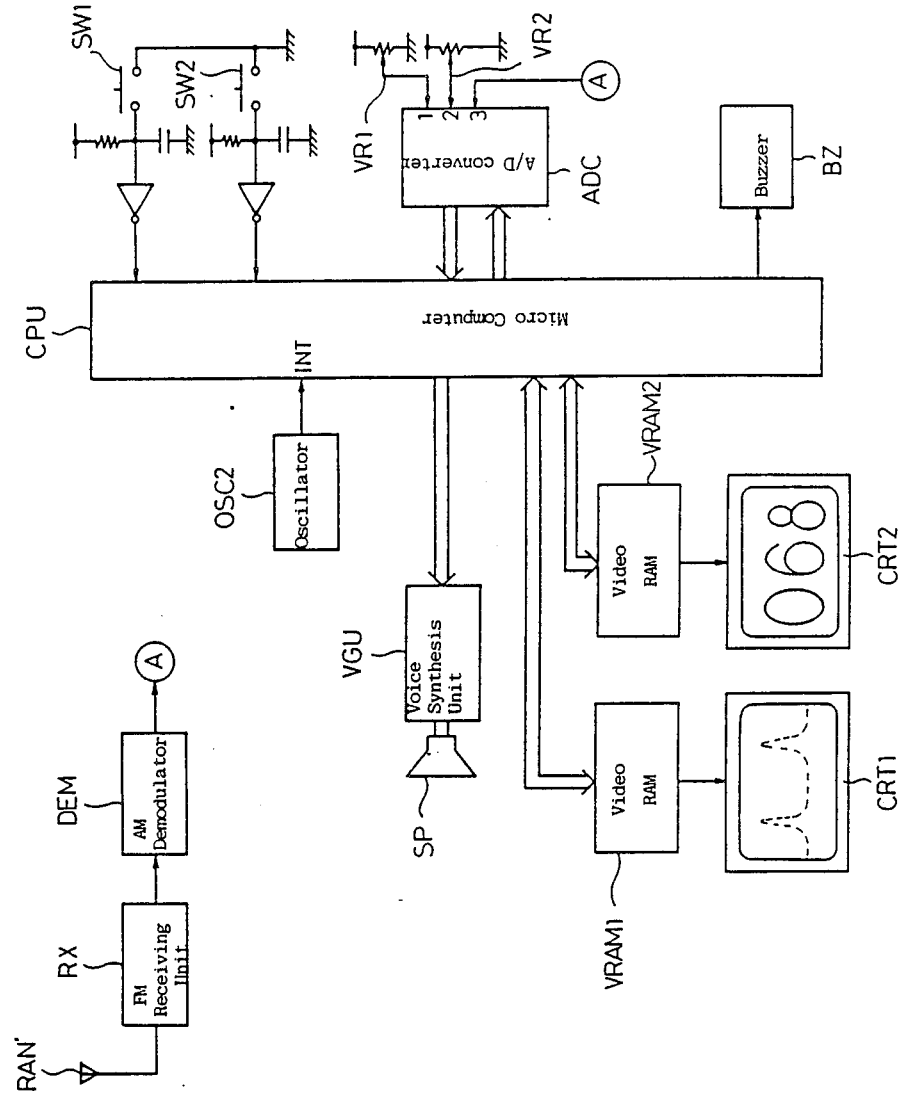

FIG. 16a shows the circuit configuration of a data receiving unit for receiving the signal from the above heartbeat detection unit (or transmitting unit 200) and for performing various processings, and FIG. 16b shows the configuration of an AM demodulator DEM shown in FIG. 16a. Referring to FIG. 16a, it is a microcomputer CPU that controls the entire circuit. Connected to the microcomputer CPU are an oscillation circuit OSC2, voice synthesis unit VGU, video memories VRAM1 and VRAM2, buzzer BZ, A/D converter ADC, key switches SW1 and SW2, etc. Circuits interposed between the key switches SW1, SW2 and the CPU is each of a waveform shaping circuit. A speaker SP is connected to an output terminal of the voice synthesis unit VGU, and Brown tube display units CRT1, CRT2 are connected to the video memories VRAM1, VRAM , respectively. Variable resistors VR1, VR2 for setting reference levels are connected to input terminals 1 and 2 of the A/D converter ADC, respectively, while an output terminal of a demodulation circuit DEM is connected to an input terminal 3 thereof.

The data receiving unit includes an FM receiver RM connected to a receiving antenna RAN. The receiving frequency of the FM receiver RX is tuned with the frequency of an electric wave radiated from the transmitting unit 200. Accordingly, an output terminal of the RM receiver RX produces the signal detected by the heartbeat detecting unit. The FM receiver RX demodulates the signal modulated in its frequency, so that the output terminal of the RX produces the 1 KHz signal modulated in its amplitude in accordance with the heartbeat signal. An AM demodulator DEM is connected to the output terminal of the FM receiver RX. As shown in FIG. 16b, the AM demodulator DEM is composed of an amplifier AM4, low pass filter LP3, amplifier AM5, low pass filter LP4, amplifier AM6, etc. An output terminal of the AM demodulator DEM produces a signal analogous to the heartbeat signal detected by the heartbeat detecting unit.

It is to be noted that the microcomputer CPU shown in FIG. 16a operates in accordance with a flow chart similar to that shown in FIG. 5 and, therefore, description will not be repeated.

Although in the foregoing embodiments the heartbeat detecting unit is positioned on the steering wheel, it may be fitted on the driver's arm. This embodiment will be described hereinafter.

Figure 17A:
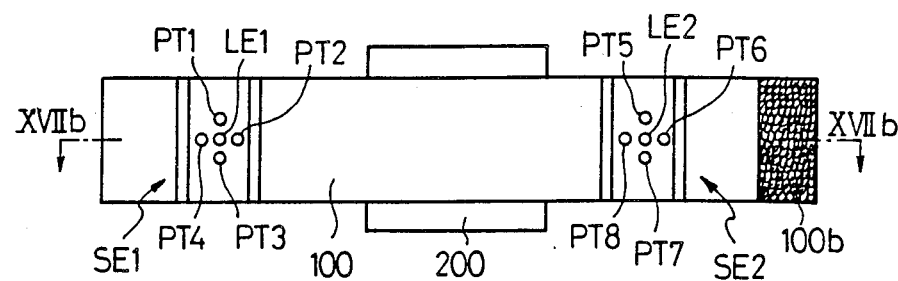
FIG. 17a is a plan view showing a heartbeat detecting unit according to another embodiment.
Figure 17B:
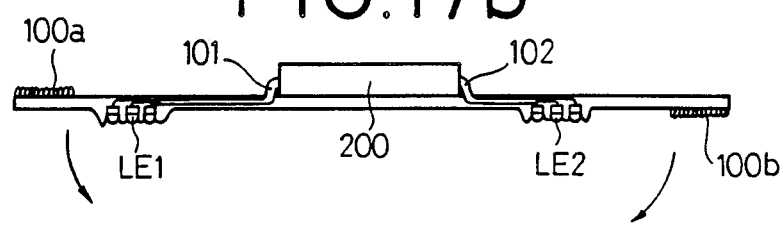
Figure 17C:
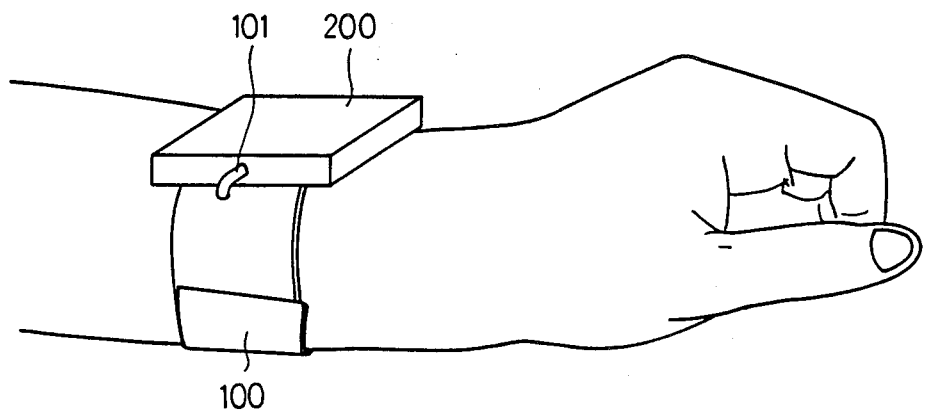
FIG. 17c is a perspective view showing the state where the heartbeat detecting unit shown in FIG. 17a is fitted to a human hand.

FIGS. 17a, 17b and 17c show an external appearance of a heartbeat detecting unit. Description will now be made with reference to these figures. This heartbeat detecting unit comprises a band-like support member 100 and a case 200 housing therein a transmitting unit. On the inner side of the support member 100, i.e., on the side coming into contact with the driver's arm, there are disposed reflection type optical sensors SE1 and SE2 spaced from each other.

Each of the optical sensors SE1 and SW2 comprises one light emitting diode LE1 (or LE2) and four photo transistors PT1, PT2, PT3 and PT4 (or PT5-PT8) arranged to surround the former. The light emitting diodes LE1 and LE2 and photo transistors PT1-PT8 are arranged to have their optical axes perpendicular to the support member 100. Stated differently, it is so arranged that, even in the state where the unit is fitted on the driver's arm as shown in FIG. 17c, the optical axes of both the light emitting diode and the photo transistors in each of the optical sensors SE1, SE2 are extended in the same direction (i.e., those optical axes become parallel to one another).

Lead wires 101 and 102 from the optical sensors SE1 and SE2 are connected to the case 200 after passing through the inside of the support member 100. The support member 100 is provided at both ends thereof with downy tapes 100a and 100b. The heartbeat detecting unit is fixed in position as shown in FIG. 17c by winding the support member 100 around the arm and then attaching the downy tapes 100a and 100b to each other.

Inside the case, similarly to the foregoing embodiment, there is housed a transmitting unit for transmitting the signal from the heartbeat detecting unit on a carrier wave. This transmitting unit has the same construction as that shown in the above embodiment (FIG. 14) except for the part relating to the connection of the sensors and, therefore, description will not be repeated.

Although in the foregoing embodiments heart rate and variance thereof are measured using the heartbeat detecting unit and the presence or absence of an anomaly is decided in accordance with the measured values, the heartbeat detecting unit can also be used to detect whether or not the driver firmly grips the steering wheel. Anomaly detection equivalent to that effected in case of measuring a heartbeat can be performed by taking a given security action in such an anomalous condition that the steering wheel is released from the driver's hands or a force of gripping the steering wheel is weakened during driving. This embodiment will be described hereinafter.

Figure 18:
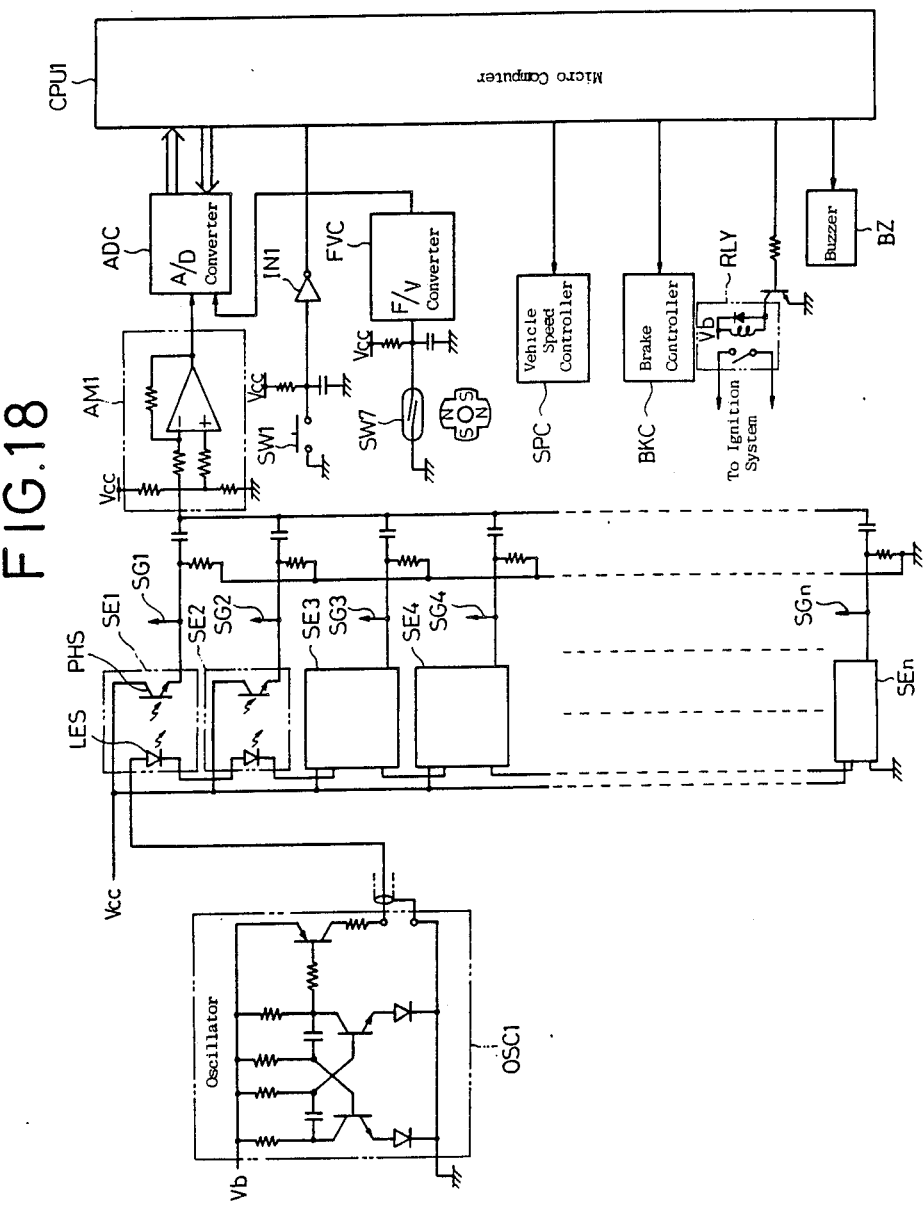
FIG. 18 is a block diagram showing the apparatus configuration according to still another embodiment.

FIG. 18 shows the configuration of the apparatus according to this embodiment. It is to be noted that the detecting section is structured similarly as shown in FIGS. 8a, 8b and 8c. Referring to FIG. 18, it is a microcomputer CPU1 that controls the entire apparatus. Connected to the microcomputer CPU1 are an analog/digital converter ADC, cancel switch SW1, freqeuncy/voltage converter FVC, vehicle speed controller SPC, brake controller BK, relay RLY, buzzer BZ, etc.

Light emitting diodes LES of the respective optical sensors SE1-SEn are connected in series, one end of which serial circuit is connected to the oscillation circuit OSC1 and the other of which is grounded. The oscillation circuit OSC1 oscillates at frequency of 1 KHz and generates voltage in the square waveform in this embodiment. But a lower level of the voltage will not be zero. Therefore, the intensity of light emitted from the light emitting diode LES of each optical sensor is varied with a period of 1 msec in a binary fashion. Output terminals of the optical sensors SE1-SEn are connected in parallel through respective capacitors and then connected to an input terminal of the amplifier AM1.

The light emitting diode LES and the photo transistor PHS of each optical sensor are arranged to have their optical axes extending in the same direction, so most parts of light emitted from the light emitting diode LES will not reach the photo transistor PHS unless there exists any obstacle crossing the direction of the optical axes, whereby the signal component of 1 KHz produced at an output terminal of the photo transistor PHS has a lower level. On the other hand, if there exists the driver's hand crossing the direction of optical axis of the optical sensor, most parts of light emitted from the light emitting diode LES is reflected by the hand and a part of the reflected light reaches the photo transistor PHS, whereby the output terminal of the photo transistor PHS produces the signal component of 1 KHz of a relatively high level.

The output terminals of respective photo transistors PHS of the optical sensors SE1-SEn are commonly connected through the capacitors for interrupting DC components and then connected to the input terminal of the amplifier AM1, as previously noted. Accordingly, a level resulted from addition of output signals from the respective optical sensors is amplified by the amplifier AM1. In other words, when the driver firmly grips the steering wheel, the driver's hand is positioned opposite to at least one optical sensor, whereby a square 1 KHz signal of a relatively large amplitude is applied to the input terminal of the amplifier AM1. Meanwhile, if the driver's hands are released from the steering wheel 4 from some anomaly, an amplitude of the 1 KHz signal component applied to the input terminal of the amplifier becomes small.

An output terminal of the amplifier AM1 is connected to one input terminal of the analog/digital converter ADC. Therefore, the microcomputer CPU1 is able to detect the presence or absence of an anomaly in the driver's condition by sampling the signal produced from the amplifier AM1 and then deciding a level of the sampled signal, i.e., an amplitude of the 1 KHz signal.

A read switch SW7 connected to an input terminal of the frequency/voltage converter FVC in turn is connected a speed meter cable on the road-vehicle and disposed near a permanent magnet rotating together with rotation of the cable, thereby applying a square signal of frequency corresponding to the vehicle speed to the frequency/voltage converter FVC. An output terminal of the frequency/voltage converter FVC is connected to another input terminal of the analog/digital converter ADC.

The vehicle speed controller SPC functions to make constant-speed control so that the vehicle speed can be maintained at a preset constant level without the need of pushing down at accelerator by the driver. In this embodiment, the microcomputer CPU1 applies a signal for releasing the constant-speed running control to the vehicle speed controller SPC. The brake controller BKC functions to actuate a braking mechanism so as to stop the road-vehicle. The microcomputer CPU1 instructs the brake controller BKC to effect braking in the given state. A contact of the relay RLY is connected to an ignition unit of an engine and, when this contact is disconnected, an ignition circuit is interrupted to stop the engine. Thus, an engine brake is applied upon disconnection of the contact of the relay RLY.

Figure 19:
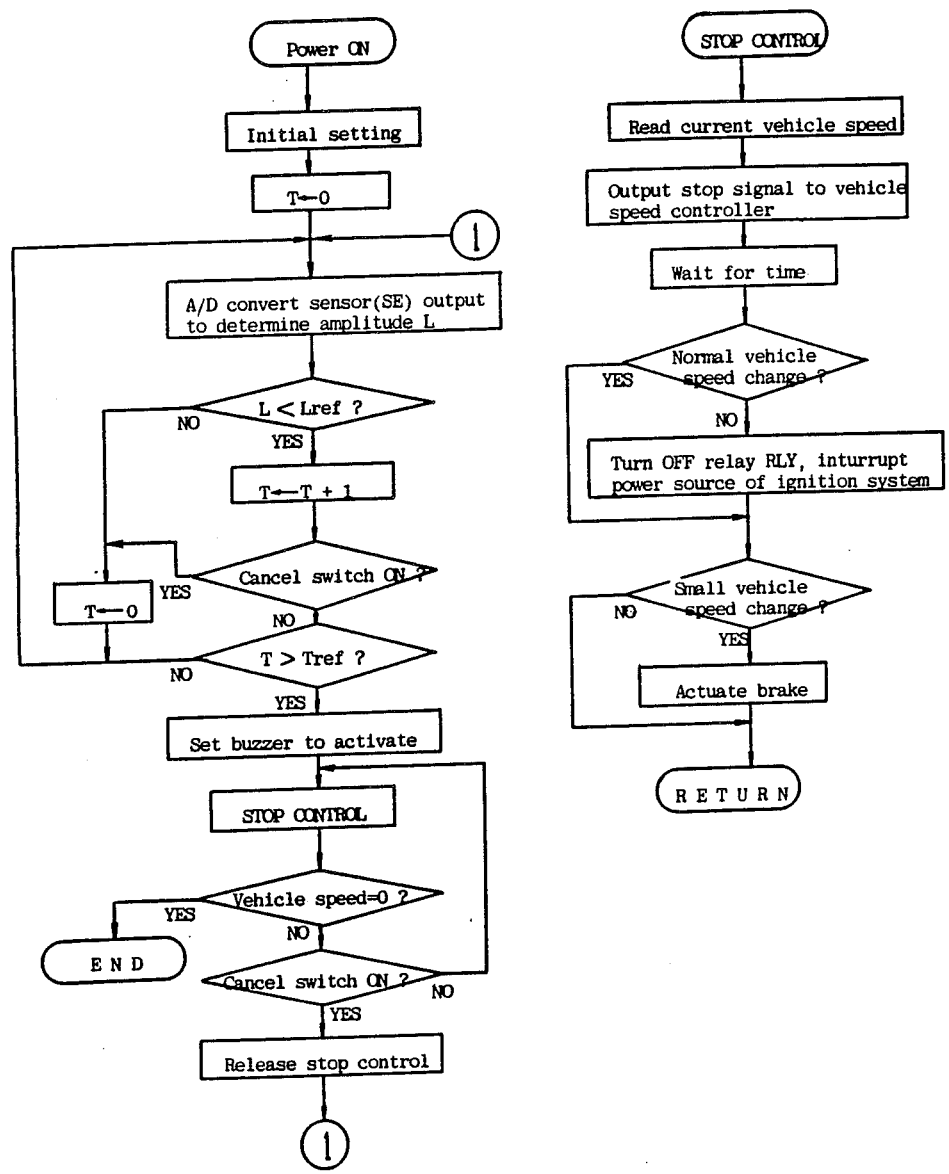
FIG. 19 is a flow chart schematically showing operation of a microcomputer CPU1 shown in FIG. 18.

FIG. 19 schematically shows operation of the microcomputer CPU1 shown in FIG. 18. Description will now be made with reference to FIG. 19. When powered on, i.e., when an ignition switch is turned on, the CPU1 first sets the states of respective output ports to initial levels and clears the memories. As a result, the contact of the relay RLY is interconnected and the engine is ready for starting. The value of 0 is set in a register T as an initial value.

An input channel of the analog/digital converter ADC is first selected to the output terminal side of the amplifier AM1, and A/D conversion is performed plural times to obtain a level change with a period of 1 msec. i.e., an amplitude L of the 1 KHz signal component. The amplitude L is compared with the preset reference value Lref and, unless L<Lref, the register T is set again to zero and the above operation will be repeated. If L<Lref is met, the content of the register is counted up by +1 and the resultant value is compared with the preset reference value Tref.

If the amplitude L becomes large or the cancel switch SW1 is turned on before T>Tref is met, the register T is set again to zero. On the other hand, if a predetermined time Tref has lapsed while keeping L<Lref, it is decided that any anomaly has occurred in the driver's condition. More specifically, if such a state that the driver's hands are released from the steering wheel 4 and the amplitude of the 1 KHz signal is reduced, has been detected continuously over a predetermined time Tref, it is decided that the driver has lost his capability of gripping the steering wheel. Upon detecting such a state, the buzzer BZ is first set to actuate and a stop control subroutine is then executed. This operation will be repeated until the vehicle speed becomes zero or the cancel switch SW1 is turned on.

In the stop control subroutine, first an input channel of the analog/digital converter ADC is set to the side of the frequency/voltage converter FVC and the vehicle speed is read. Then, a stop instruction signal is applied to the vehicle speed controller SPC. The CPU1 waits for a given time and checks during such a time whether or not there has occurred a vehicle speed change (vehicle speed reduction) larger than a predetermined amount. Stated differently, it is monitored whether or not the vehicle speed is normally lowered, because the vehicle speed can not be lowered even with the vehicle speed controller SPC receiving an instruction to release the constant-speed control, if the driver's foot is put on the accelerator pedal in the state where the vehicle speed controller SPC is free of constant-speed control.

If the vehicle speed is not normally lowered, the contact of the relay RLY is controlled to turn off, whereby the source power to the ignition system is interrupted to forcibly apply the engine brake. Further, if a change in vehicle speed is smaller than a predetermined amount, the brake controller BKC is instructed to actuate the braking mechanism. When the cancel switch SW1 is turned on during the stop control, the stop control operation is released.

Figure 20:
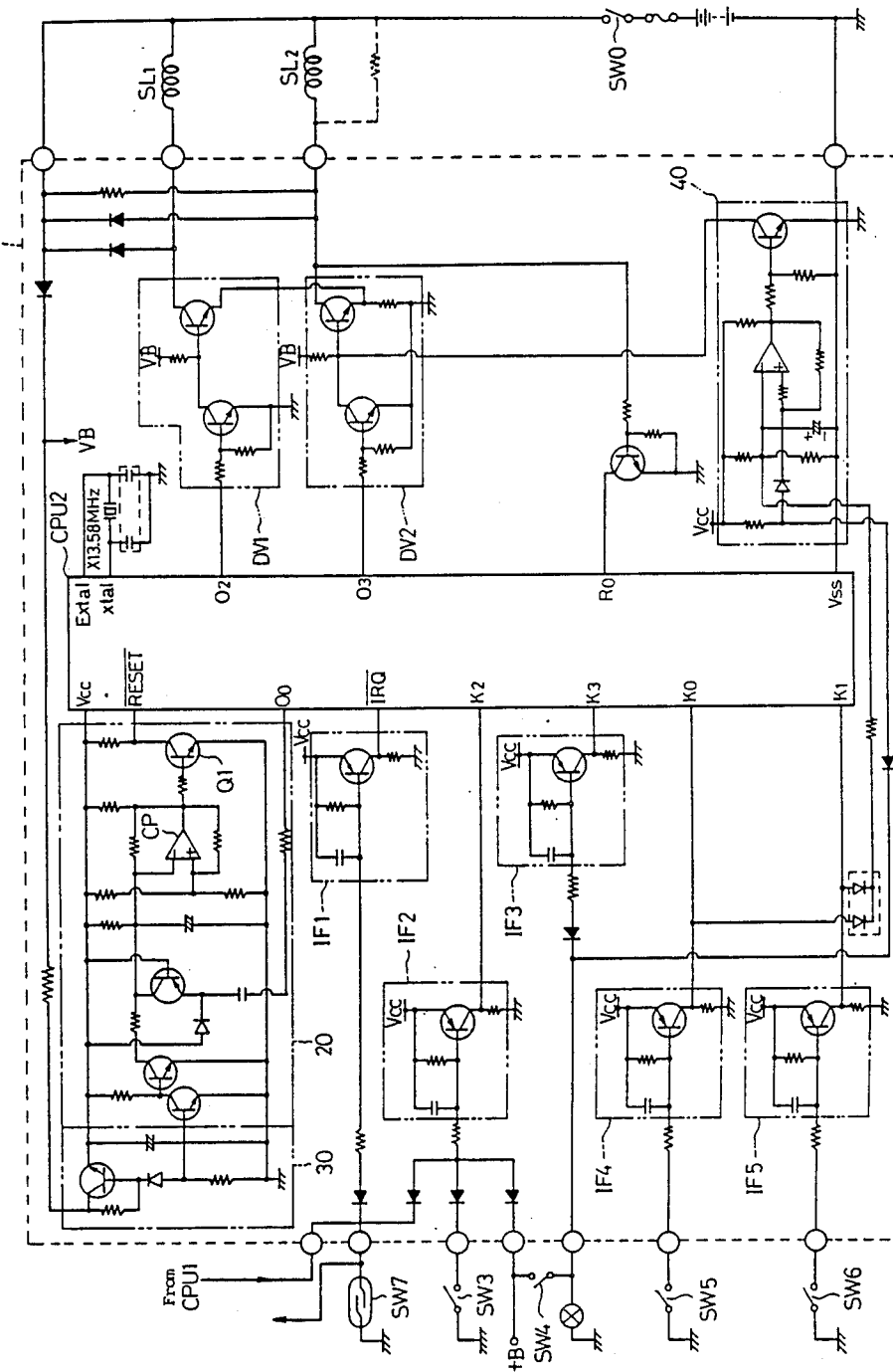
FIG. 20 is an electric circuit diagram showing the configuration of a vehicle speed controller SPC shown in FIG. 18.
Figure 21:
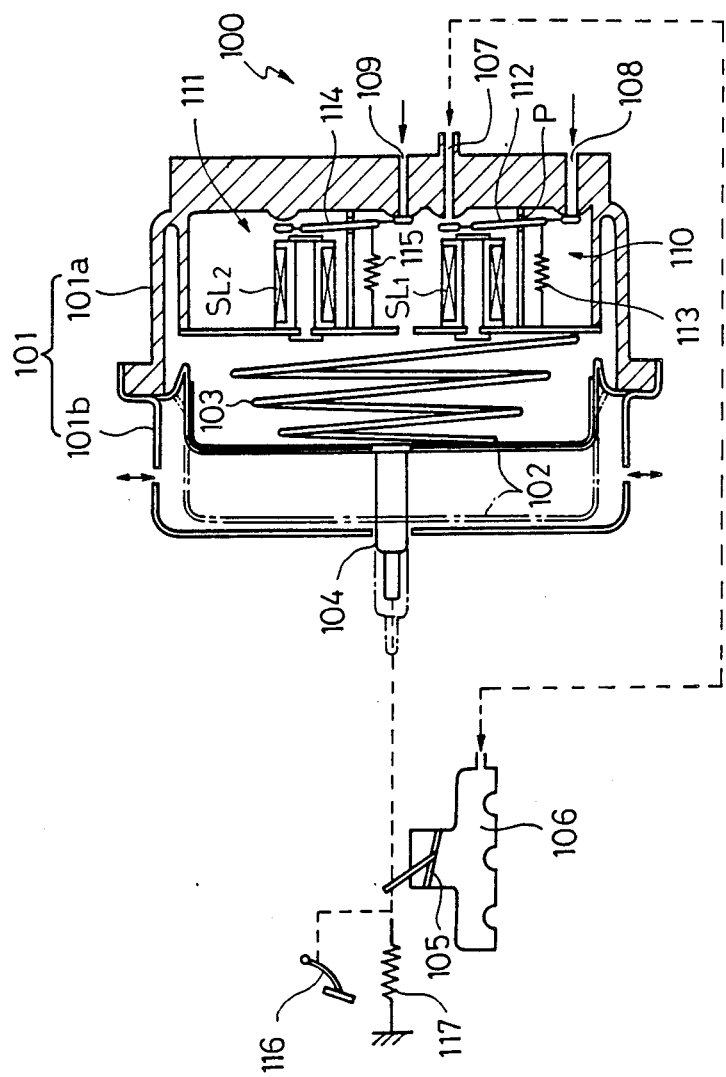
FIG. 21 is a longitudinal sectional view showing a negative pressure actuator connected to the controller shown in FIG. 20.

FIG. 20 shows the configuration of an electric circuit of the vehicle speed controller SPC shown in FIG. 18, FIG. 21 shows the structure of a throttle driving system, and FIGS. 22a, 22b, 22c, 22d and 22e schematically show operation of a microcomputer CPU2 shown in FIG. 20. First, the circuit configuration of the vehicle speed controller SPC will be described with reference to FIG. 20.

An electronic controller 10 is mainly composed of a single-chip microcomputer CPU2 in this embodiment. A runaway detecting circuit 20 is connected to a reset port RESET of the CPU2, and a vehicle speed detecting reed switch SW7, clutch switch SW3, stop switch SW4, set switch SW5 and a resume switch SW6 are connected to an external interruption input port IRQ and input ports K2, K3, K0 and K1 through interface circuits IF1, IF2, IF3, IF4 and IF5, respectively. Further, a signal line led from the output port of the microcomputer CPU1 for the unit for detecting grasp of the steering wheel is connected in parallel to the clutch switch SW3 through a diode.

In this embodiment, when the contact of the vehicle speed detecting reed switch SW7 is turned from a closed state to an opened state, an output level of the interface circuit IF1 becomes a low level L, thus applying an interrupt request to the microcomputer CPU. The clutch switch SW3 is opened and closed in an interlock relation with a clutch pedal of the road-vehicle, and the stop switch SW4 is opened and closed in an interlock relation with a brake pedal of the road-vehicle. Connected to the stop switch SW4 is a stop lamp, which is lit up upon turning-on (closing) of the SW4.

Both the set switch SW5 and the resume switch SW6 are of push button switches and disposed on an instrument panel at such a position as allowing the driver to easily operate those switches.

An output port Oo of the microcomputer CPU2 is connected to the runaway detecting circuit 20, while drivers DV1 and DV2 are connected to output ports O2 and O3, respectively. Connected to an output of the driver DV1 is a control solenoid SL1 for controlling a negative pressure actuator later described, and connected to an output of the driver DV2 is a release solenoid SL2.

Voltage from a battery loaded on the road-vehicle is applied through an ignition switch SW0 to the control solenoid SL1, release solenoid SL2 and a constant-voltage power supply circuit 30 for generating constant voltage Vcc. A circuit 40 is provided to deenergize the release solenoid SL2 independently of operation of the CPU2, when an brake is applied.

FIG. 21 shows the structure of a negative pressure actuator 100 controlled by the electric circuit shown in FIG. 20. Description will now be made with reference to FIG. 21. A housing 101 is composed of two halves 101a and 101b. A diaphragm 102 is held between the flanged portions of those two halves 101a and 101b. A space defined by the diaphragm 102 and the housing half 101a serves as a negative pressure chamber, while a space defined by the diaphragm 102 and the housing half 101b is communicated with the atmosphere. Designated at 103 is a compression coil spring interposed between the housing half 101a, which spring pushes the diaphragm 102 back to such a position as shown by phantom lines, when the pressure in the negative pressure chamber nearly equal to the atmospheric pressure. A projection 104 fixed to the nearly center of the diaphragm 102 is connected to a link of a throttle valve 105. The housing half 101a is formed with a negative pressure intake port 107 in communication with an intake manifold 106, and with atmosphere intake ports 108 and 109.

Designated at 110 is a negative pressure control valve and at 111 is a negative pressure release valve, which are both fixed to the housing half 101a. A movable piece 112 of the negative pressure control valve 110 is capable of tilting about A as a fulcrum, and it has one end connected to a tension coil spring 113 and the other end opposite to the control solenoid SL1. Both ends of the movable piece 112 function as valve bodies, causing the negative pressure intake port 107 to open and the atmosphere intake port 108 to close (the state as shown in the figure) or causing the negative pressure intake port 107 to close and the atmosphere intake port 108 to open in accordance with energization of deenergization of the solenoid SL1.

The negative pressure release valve 111 also has a movable piece 114, tension coil spring 115 and the solenoid SL2 similarly to the valve 110, but the movable piece 114 functions to just close the atmosphere intake port 109 (the state as shown in the figure) or open the same. It is to be noted that designated at 116 is an accelerator pedal and at 117 is a tension coil spring.

Operation of the microcomputer CPU2 shown in FIG. 20 will now be described with reference to FIGS. 22a, 22b, 22c, 22d and 22e. It is to be noted that, while the road-vehicle is running, the reed switch SW7 is repeatedly turned on/off at all times and the microcomputer CPU2 implements the external interrupt processing shown in FIG. 22d every when the switch SW2 is turned off.

When powered on, the CPU2 first makes initial setting. In other words, it sets the respective output ports to initial levels and clears the content of each memory.

Then, the level of the output port Oo is inverted. More specifically, when the output port Oo has been set to a high level H, the level is now set to a low level L, and when it has been set to a low level L, the level is now set to a high level H. It is arranged that the above processing is always implemented at least once within a predetermined period of time, the CPU2 is under normal operation. As a result, a pulse signal with an almost constant period is applied to the runaway detecting circuit 20 from the CPU2. When the pulse signal is applied to the runaway detecting circuit 20, an output level of a comparator CP is set to H and a transistor Q1 is turned on, thereby maintaining the RESET terminal of the CPU2 at a high level H. In the event there occurs no pulse at the output port Oo from runaway of the CPU2 or other reasons, the output level of the comparator CP is inverted to L and the transistor Q1 is turned off, thereby applying a low level L to the RESET terminal of the CPU2. The CPU2 performs the same operation as that effected at the time of power-on when the RESET terminal is set to L, so that runaway is stopped.

Under normal operation, the CPU2 reads levels at the input ports K0, K1, K2 and K3, and it discriminates operations of the switches or so and then executes the processing in accordance with the discriminated switch as follows.

When there is no change in inputs (except for the case that the timer, flag, etc. is set), the CPU2 implements a processing loop in which it passes through steps S2 - S3 S4 - S42 - S43, executes a plural-storage routine shown in FIG. 22c and then returns again to the step S2. At this time, the contents of the vehicle speed memory, target value register, flags, etc. remain unchanged.

In case that the clutch switch SW3 or the stop switch SW4 is turned on, that the vehicle speed is less than a given level (e.g., 30 Km/h), or that a stop signal is applied from the CPU1, the levels at the output ports are set to not energize the solenoids and the content of the target value register R0 is cleared to release the constant-speed control. At the same time, flags or so are all cleared. This clears a constant-speed running mode when it has been set. Further, the release solenoid SL2 is deenergized to operate the negative pressure actuator 100 in such a direction that the throttle valve is closed quickly. Next, the CPU2 proceeds to step S61 and then returns back to step S2 after passing the plural-storage routine.

When the set switch SW5 is turned on, at the first time the CPU2 proceeds through steps S9 - S17 - S18 - S19 - S20, sets a set-on flag SET-ON to "1", and then sets the control solenoid controlling duty to 5%. At the control solenoid controlling duty of 5%, since a proportion of time in which negative pressure control valve 110 allows the inside of the negative pressure actuator 100 to communicate with the atmosphere is increased, the negative pressure actuator 110 is moved in such a direction that the throttle valve closes, so that the vehicle speed is lowered with a lapse of time. Actual driving of the control solenoid is made in step S43 in accordance with the preset duty. In the state where the set switch SW5 is depressed, the CPU2 proceeds through steps S61 - S62 - S81 . . . while passing the plural-storage routine, and then again proceeds through steps S2 - S3 . . . S9 - S17 - S18 - S61.

When the set switch SW5 is turned off, the CPU2 proceeds through steps S9 - S10 - S11 - S12 - S13 - S14, clears the set-on flag SET-ON (to "0") and then sets a set-off flag SET-OFF to 1. Subsequently, it proceeds to step S61, passes through steps S67 - S68 - S69 - S70 - S81 . . . because the set-off flag SET-OFF is set to 1, increment the content of a counter (pointer) RA for specifying the vehicle speed memory (within a range not exceeding 3), and then clears and starts a one-second timer for setting. After completion of this processing, the set-off flag SET-OFF is cleared to "0". In other words, steps of S67, S68, S69 and S70 are implemented only in the first time processing after the set switch SW5 has been turned off. From the subsequent time, it proceeds through steps S61 - S62 - S63 . . .

If the set switch SW5 will not be turned on in one second after it has been turned off, it is checked in step S63 that the preset time is over and, if so, the CPU2 proceeds through steps S64 - S65 - S66. This causes the content of the target value register R0 to be stored in the vehicle speed memory designated by the content of the counter RA and, after implementing a throttle initializing routine later described, the operation mode is set to a constant-speed control mode.

Since the target value register R0 stores therein the vehicle speed at the time when step 14 was implemented, i.e., at the moment when the set switch SW5 was turned off, the vehicle speed at that time is loaded into the given memory. If the set switch SW5 is repeatedly turned on/off two times, for example, until it will have been finally turned off (remains for one second), the processing step of S67 - S68 - S69 - S70 is implemented two times during such a period of time and hence the content of the counter RA assumes 2, so that the content of the target value register R0 is stored in the vehicle speed memory 2. In this embodiment, since there are three speed vehicle memories, step 67 is provided to prevent the value of the counter RA from exceeding three. Accordingly, even if the set switch SW5 is turned on/off continuously three or more times, the vehicle speed memory 3 is selected. Coming into a constant-speed control mode, the CPU2 proceeds through steps S40 - S41 - S42 and, every when implementing this processing, the control solenoid controlling duty is so reset that the content of the target value register R0, i.e., the stored vehicle speed, becomes equal to the current vehicle speed. If the set switch SW5 remains depressed, the vehicle speed is gradually lowered, because the control duty continues to be set at 5% in step S20.

When the resume switch SW6 is turned on, at the first time the CPU2 proceeds through steps S31 - S44 - S45 - S46 - S47 - S48 - S43, sets a resume-on flag RESUME-ON to "1", and then clears and starts a 0.9 timer for resuming. Next, it implements a processing loop passing through S61 - S81 - S82 - S2. If the resume switch SW6 continuously remains depressed (on) for 0.9 second, it is detected in step S48 that the preset time is over, and the CPU2 proceeds to S49 where the control solenoid controlling duty is set to 90%. In the state where the control solenoid controlling duty is at 90%, a proportion of time in which the negative pressure control valve 110 communicates the inside of the negative pressure actuator 100 with a negative pressure source (or intake manifold). As a result, the negative pressure actuator 110 is moved in such a direction the throttle valve opens, so that the vehicle speed is increased with a lapse of time.

When the resume switch SW6 is turned off, the CPU2 first proceeds through steps S31 - S32 - S33 - S34 - S35 - S46 . . . , clears the resume-on flag RESUME-ON to "0", and then sets a resume-off flag RESUME-OFF to "1". If the resume switch SW6 is turned on for a long time and the 0.9 second timer is up, the CPU2 proceeds through steps S36 - S37 - S38 - S39 and, in a similar way to the case that the set switch SW5 is turned on/off, it loads the current vehicle speed in the target value register R0 and the content of the target value register is stored in the vehicle speed memory designated by the content of the register R0. Further, the resume-off flag RESUME-OFF is cleared to "0" so as to avoid that the normal resuming operation will not be run in the plural-storage routine.

If the resume switch SW6 is turned off before the 0.9 second timer will have been up, the CPU2 proceeds through steps S81 - S87 - S88 - S89 - S90 because the resume-off flag RESUME-OFF is set at "1", increments the content of the counter RA, clears and starts the 1 second timer for resuming, and then clears the resume-off flag RESUME-OFF to "0". The processing step of S81 - S87 - S88 - S89 - S90 is implemented once during the time when the resume-off flag RESUME-OFF is at "1", i.e., every when the resume switch is turned from an on-state to an off-state. Accordingly, the counter RA stores therein the number of how much the resume switch has been turned from an on-state to an off-state.

When one second has lapsed after the resume switch SW6 was turned off, the CPU2 proceeds through steps S81 - S82 - S83 - S84 - S85 - S86 because the 1 second timer for resuming is up, and then the content of the vehicle speed memory designated by the content of the counter RA, for example, the content of the vehicle speed memory 3 in case the resume switch SW6 is turned on/off three times, is stored in the target value register R0. And the CPU2 implements a throttle initializing routine S86 and sets a constant-speed control mode. Coming into a constant-speed control mode, it proceeds through steps S40 - S41 - S42 - S43 and updates the control solenoid controlling duty such that the current vehicle speed approaches the content of the target value register.

Figure 22A:
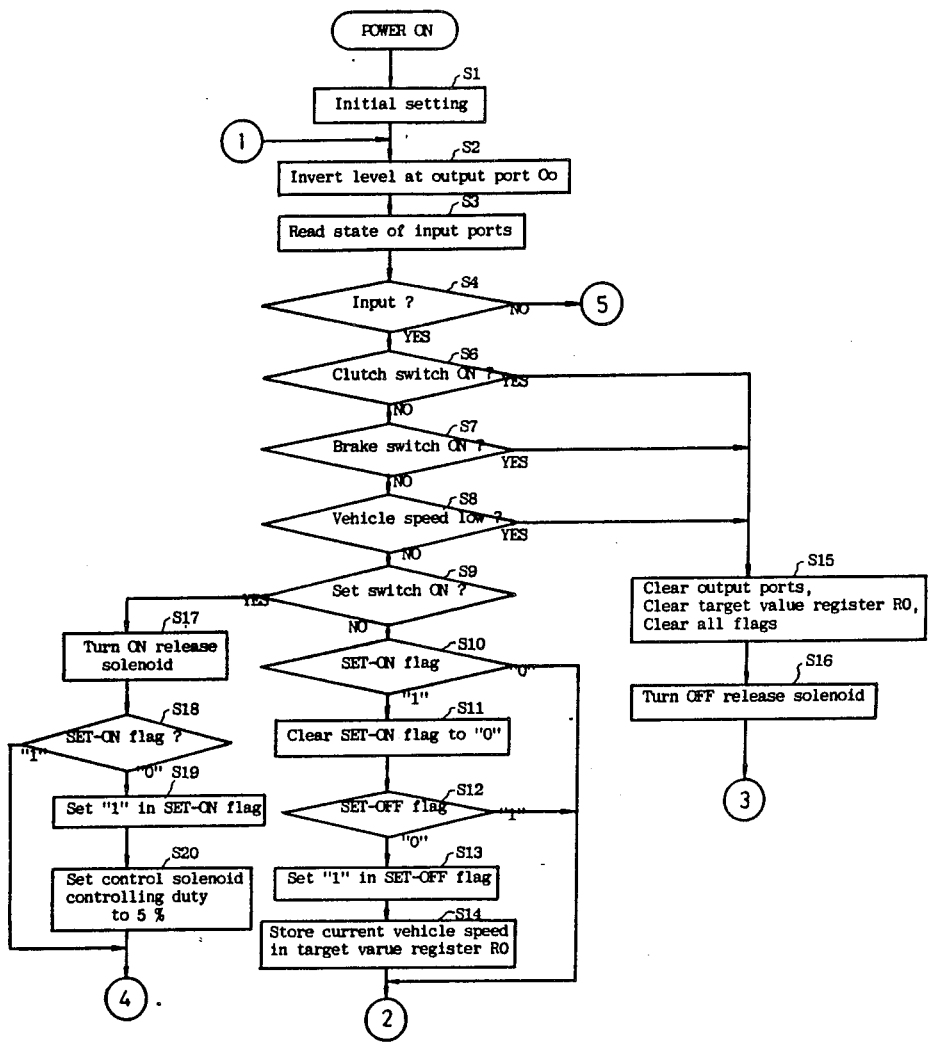
FIGS. 22a, 22b, 22c, 22d and 22e are flow charts schematically showing operation of a microcomputer CPU2 shown in FIG. 21.
Figure 22B:
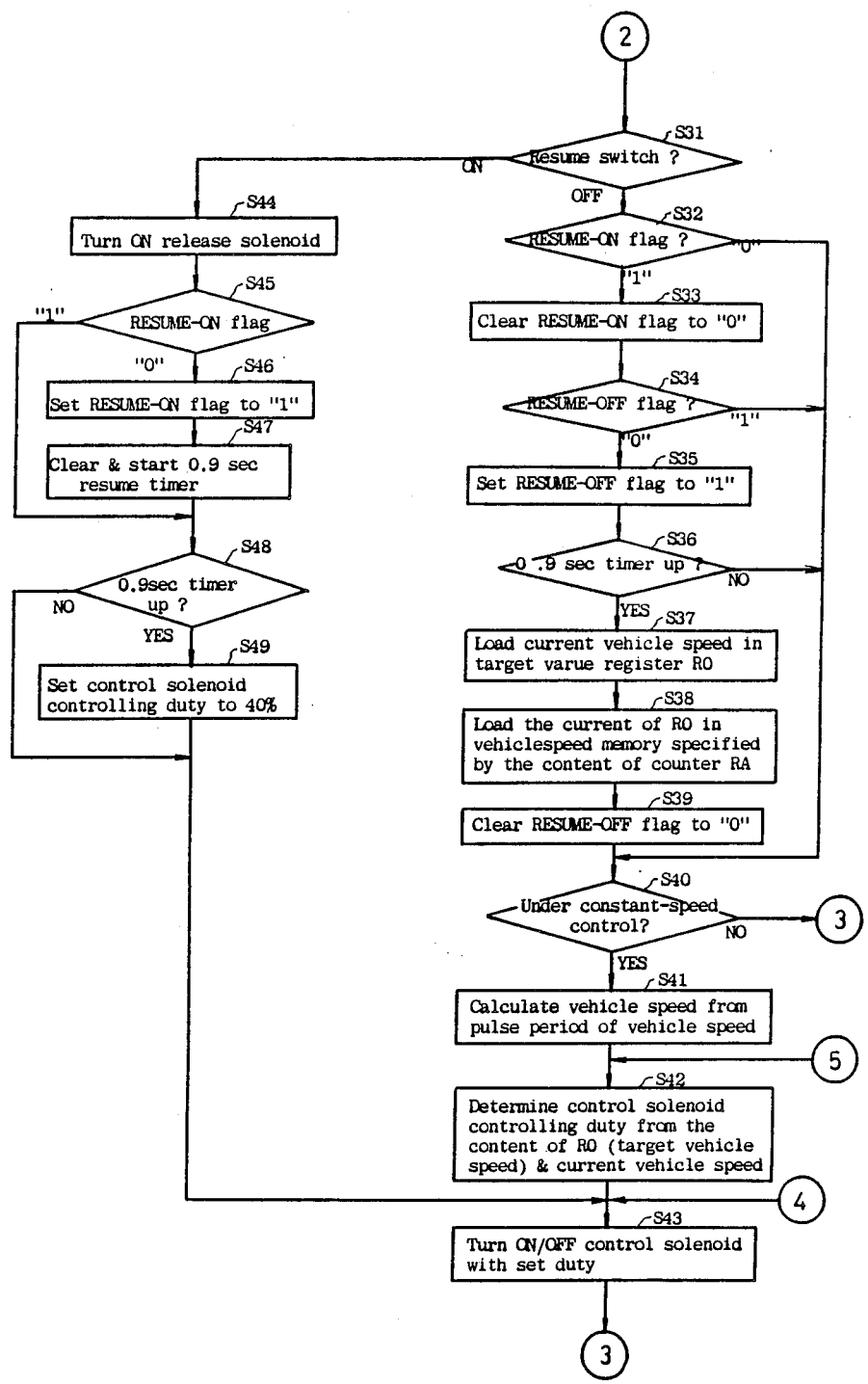
Figure 22C:
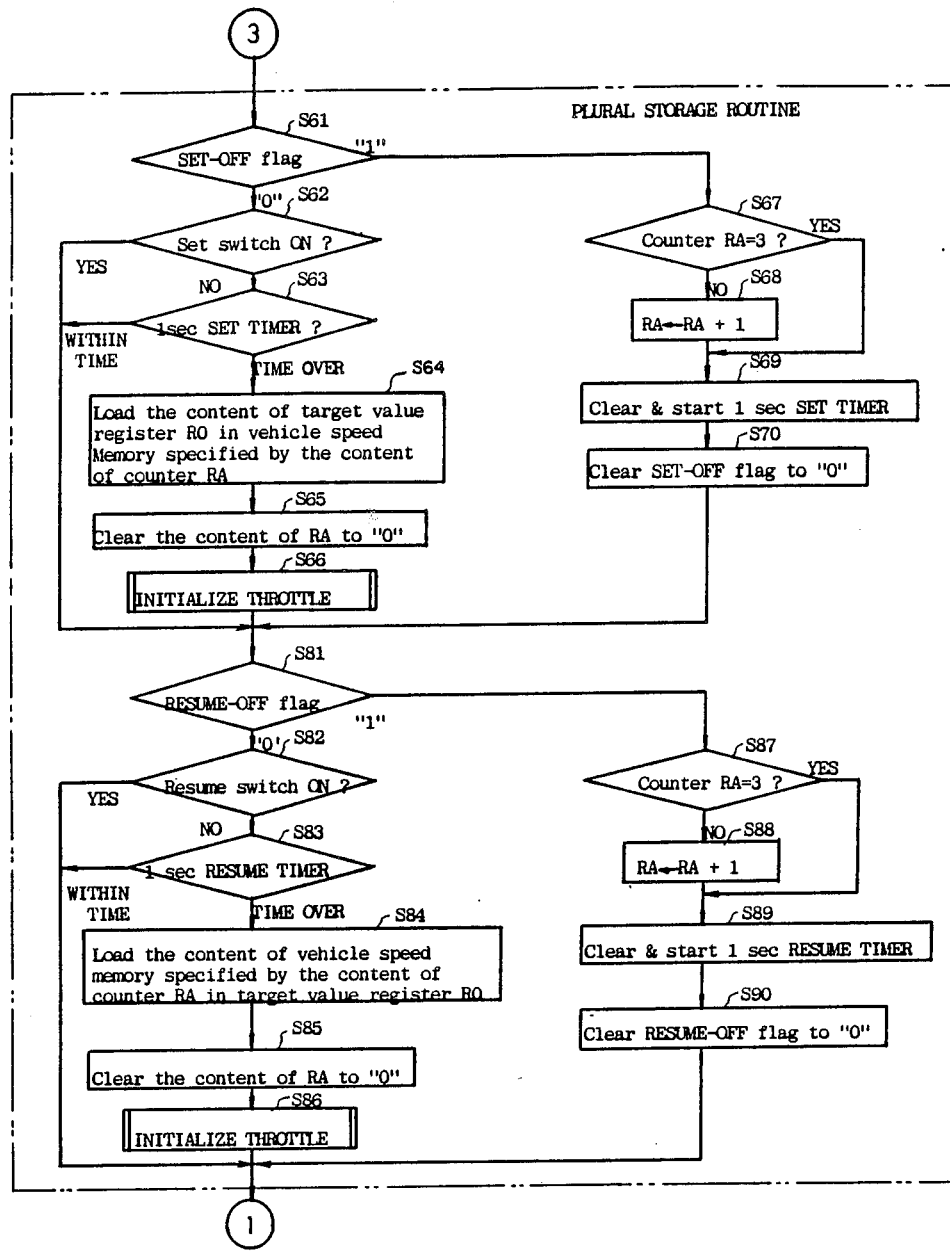
Figure 22E:
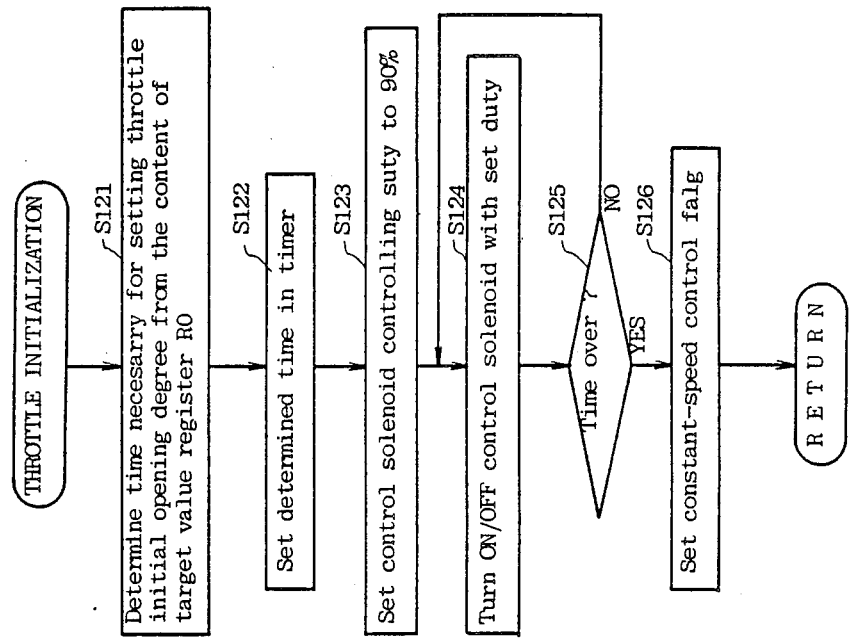

The throttle initializing routine will now be described with reference to FIG. 22a. In short, this processing is intended to make anticipatory control (i.e., open loop control) in order that the negative pressure actuator 100 is quickly driven to a given position (i.e., throttle initial opening position). More specifically, the control solenoid controlling duty is set to a high value (90%), a period of time in which the above state is to be continued is previously calculated based on the content of the target value register R0 and then set in a timer, and the 90% duty control is continued until the set time is over. When the set time is over, a constant-control flag is set to establish a constant-speed mode.

Figure 22D:
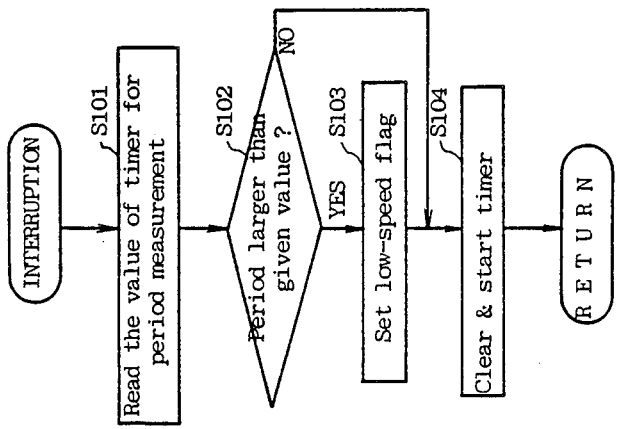

The external interrupt processing will be described with reference to FIG. 22d. This processing is intended to determine an on/off period of the vehicle speed detecting reed switch SW7. Every when the processing is implemented or the SW7 is turned off, the CPU2 reads the counted value of an internal timer and then clears and starts the timer. If the counted value of the timer is higher than a predetermined amount (i.e., if the vehicle speed is less than a given level), a low-speed flag is set. When the low-speed flag is set, it proceeds from step S8 in the main routine to step S15, thereby releasing a constant-speed control mode similarly to the case that the clutch pedal or brake pedal is operated.

Although in the above embodiment the throttle valve, brake and ignition system are controlled to stop the road-vehicle upon detecting the fact that the driver's hands are released from the steering wheel, there is a fear that the steering wheel may be erroneously steered depending on the road condition and the road-vehicle may be abruptly changed in its running direction, if an brake is applied in the state where the steering is not firmly gripped. In such a case, it is possible to adopt the arrangement that the steering wheel is braked or locked to prevent the same from moving in a large extent. Further, although in the above embodiment an accelerator pedal 116 is always connected to the throttle valve, an electromagnetic clutch may be proviced between the accelerator pedal and the throttle valve to be disconnected in the event grasp of the steering wheel can not be detected, in order that the throttle valve will be returned even if the driver is fallen down while treading on the accelerator pedal.

Having now fully set forth both structure and operation of preferred embodiments of the concept underlying the present invention, various other embodiments as well as certain variations and modifications of the embodiments herein shown and described will obviously occur to those skilled in the art upon becoming familiar with the underlying concept. It is to be understood, however, that with the scope of the appended claims, the invention may be practiced otherwise than as specifically set forth herein.

What is claimed is:

1. A human condition monitoring and security controlling apparatus on road vehicles having a steering wheel comprising:
   a plurality of status detecting means, each means including an optical sensing means for generating an electric signal in accordance with whether or not said steering wheel of the road vehicle is firmly gripped, said optical status detecting means being disposed on the steering wheel with given intervals therebetween;
   detection energizing means for energizing said status detecting means;
   signal processing means for processing an electric signal from said status detecting means;
   at least one security means carried by the road vehicle; and
   electronic control means for monitoring information output from said signal processing means and for energizing said security means if any anomaly occurs wherein said electronic control means sequentially selects said light receiving means, detects differences in output signal level between every adjacent light receiving means, and specifies those light receiving means in accordance with said differences.

2. A human condition monitioring and security controlling apparatus on road vehicles according to claim 1 wherein said optical sensing means is comprised of a light emitting means and a light receiving means receiving light from the former.

3. A human condition monitoring and security controlling apparatus on road vehicles according to claim 2 wherein said light receiving means is disposed in the vicinity of said light emitting means to have its optical axis extending substantially in the same direction as that of said light emitting means.

4. A human condition monitoring and security controlling apparatus on road vehicless according to claim 2 wherein detection energizing means includes oscillation means for imparting periodic fluctuations to said light emitting means and wherein said electronic control means detects the magnitude of amplitude of an output signal from said light receiving means.

5. A human condition monitoring and security controlling apparatus on road vehicles according to claim 2 wherein said signal processing means includes a filter means.

6. A human condition monitoring and security controlling apparatus on road vehicles according to claim 1 wherein said security means carried by the road vehicle includes alarm sound generating means.

7. A human condition monitoring and security controlling apparatus on road vehicles according to claim 1 wherein said security means carried by the road vehicle includes speed regulating means for lowering the speed of the road vehicle.

8. A human condition monitoring and security controlling apparatus on road vehicles having a steering wheel comprising:
   a plurality of heartbeat detecting means each comprising at least one light emitting means and at least one light receiving means disposed in the vicinity of the light emitting means on said steering wheel, said detecting means being disposed with given intervals therebetween with the optical axes thereof extending above said steering wheel;
   detection energizing means for energizing said heart beat detecting means;
   signal processing means for processing an electric signal from said heartbeat detecting means;
   at least one security means carried by said road vehicle; and
   electronic control means for monitoring a heartbeat signal output from said signal processing means and for energizing said security means if any anomaly occurs wherein said electronic control means sequentially selects said light receiving means, detects differences in output signal level between every adjacent light receiving means, and specifies those light receiving means in accordance with said differences.

9. A human condition monitoring and security controlling apparatus on road vehicles according to claim 8 wherein said electronic control means calculates at least a value corresponding to fluctation in periods of the heartbeat signal and detects any anomaly in accordance with the value.

10. A human condition monitoring and security controlling apparatus on road vehicles according to claim 8 wherein said heartbeat detecting means is disposed on a steering wheel of the road vehicle.

11. A human condition monitoring and security controlling apparatus on road vehicles according to claim 8 wherein said heartbeat detecting means is mounted on a band shaped support member.

12. A human condition monitoring and security controlling apparatus on road vehicles according to claim 8 wherein said each heartbeat detecting means is comprised of light emitting means and a plurality of light receiving means arranged in the vicinity of said light emitting means to surround the same and to have their optical axes extending substantially in the same direction.

13. A human condition monitoring and security controlling apparatus on road vehicles according to claim 8 wherein said detection energizing means includes oscillation means for imparting period fluctuations to said light emitting means, and wherein said signal processing means includes heartbeat signal demodulating means for demodulating a modulated signal from said light receiving means.

14. A human condition monitoring and security controlling apparatus on road vehicles according to claim 8 wherein said signal processing means includes signal transmitting means for outputting an electric wave modulated with an electric signal from said light receiving means, and signal, receiving means for receiving said electric wave and demodulating the same to obtain the electric signal from said light receiving means.

15. A human condition monitoring and security controlling apparatus on road vehicles according to claim 14 wherein said detecting energizing means and said signal transmitting means are detachably secured to spokes of said steering wheel.

16. A human condition monitoring and security controlling apparatus on road vehicles comprising:
- a plurality of heartbeat detecting means each comprising at least one ligth emitting means and at least one light receiving means disposed in the vicinity of the light emitting means;
- detection energizing means for energizing said heart beat detecting means;
- signal processing means for processing an electric signal from said heartbeat detecting means;
- at least one security means carried by said road vehicle; and
- electronic control means for monitoring a heartbeat signal output from said signal processing means and for energizing said security means if any anomaly occurs wherein said electronic control means sequentially selects said light receiving means, detects differences in output signal level between every adjacent light receiving means, and specifies those light receiving means in accordance with said differences.

* * * * *